(12) United States Patent
Murdeshwar et al.

(10) Patent No.: US 12,109,136 B2
(45) Date of Patent: Oct. 8, 2024

(54) DEVICES AND METHODS TO TREAT AND PREVENT DIVERTICULITIS

(71) Applicant: GYRUS ACMI, INC., Southborough, MA (US)

(72) Inventors: Nikhil M. Murdeshwar, Maple Grove, MN (US); Thomas J. Holman, Princeton, MN (US)

(73) Assignee: Gyrus ACMI, Inc., Westborough, MA (US)

( * ) Notice: Subject to any disclaimer, the term of this patent is extended or adjusted under 35 U.S.C. 154(b) by 822 days.

(21) Appl. No.: 17/185,592

(22) Filed: Feb. 25, 2021

(65) Prior Publication Data
US 2021/0259864 A1 Aug. 26, 2021

Related U.S. Application Data

(60) Provisional application No. 63/116,681, filed on Nov. 20, 2020, provisional application No. 62/981,369, filed on Feb. 25, 2020.

(51) Int. Cl.
*A61F 2/962* (2013.01)
*A61B 17/00* (2006.01)
(Continued)

(52) U.S. Cl.
CPC ........ *A61F 2/962* (2013.01); *A61B 17/00234* (2013.01); *A61F 2/82* (2013.01);
(Continued)

(58) Field of Classification Search
CPC ............ A61B 17/00234; A61K 9/0009; A61K 9/0019; A61K 9/1676; A61M 31/00; A61F 2/962; A61F 2/82; A61F 2/95
See application file for complete search history.

(56) References Cited

U.S. PATENT DOCUMENTS

| | | |
|---|---|---|
| 5,100,419 A | 3/1992 | Ehlers |
| 6,086,585 A | 7/2000 | Hovda et al. |

(Continued)

FOREIGN PATENT DOCUMENTS

EP 1880686 B1 6/2017

OTHER PUBLICATIONS

"U.S. Appl. No. 17/185,610, Non Final Office Action mailed Feb. 27, 2024", 14 pgs.
(Continued)

*Primary Examiner* — Dung T Ulsh
(74) *Attorney, Agent, or Firm* — Schwegman Lundberg & Woessner, P.A.

(57) ABSTRACT

A method of treating diverticulitis while maintaining the bioactivity of the diverticulum. The devices and methods include placing an endoscopic device within a colonic lumen relative to at least one diverticulum and inserting a plurality of particles into the at least one diverticulum. The plurality of particles can include magnetic particles, non-magnetic particles, or both. The plurality of particles can partially or totally occlude the diverticulum preventing unwanted material from entering the diverticulum. Additionally, the plurality of particles can include antimicrobial and therapeutic layers that can treat diverticulitis and prevent or minimize diverticulitis from occurring.

20 Claims, 13 Drawing Sheets

(51) Int. Cl.
*A61B 17/12* (2006.01)
*A61B 18/00* (2006.01)
*A61F 2/82* (2013.01)
*A61F 2/95* (2013.01)
*A61K 9/00* (2006.01)
*A61K 9/16* (2006.01)
*A61K 33/38* (2006.01)
*A61K 45/06* (2006.01)
*A61M 31/00* (2006.01)

(52) U.S. Cl.
CPC .............. *A61F 2/95* (2013.01); *A61K 9/0009* (2013.01); *A61K 9/0019* (2013.01); *A61K 9/1676* (2013.01); *A61K 33/38* (2013.01); *A61K 45/06* (2013.01); *A61M 31/00* (2013.01); *A61B 2017/00278* (2013.01); *A61B 2017/00818* (2013.01); *A61B 2017/12018* (2013.01); *A61B 2018/00291* (2013.01); *A61B 2018/00494* (2013.01); *A61B 2217/005* (2013.01); *A61B 2217/007* (2013.01); *A61F 2210/0014* (2013.01); *A61F 2210/0076* (2013.01); *A61F 2220/005* (2013.01); *A61M 2202/0007* (2013.01); *A61M 2202/06* (2013.01)

(56) References Cited

U.S. PATENT DOCUMENTS

| | | |
|---|---|---|
| 6,425,854 B1 | 7/2002 | Galt et al. |
| 9,084,605 B2 | 7/2015 | Hawkins et al. |
| 9,955,974 B2 | 5/2018 | Adam |
| 2004/0073247 A1 | 4/2004 | Loshakove et al. |
| 2010/0015200 A1 | 1/2010 | McClain et al. |
| 2011/0277777 A1* | 11/2011 | Alexander ....... A61B 17/12113 128/898 |
| 2013/0158465 A1 | 6/2013 | Bates et al. |
| 2015/0209109 A1* | 7/2015 | Rege ...................... A61B 18/18 604/20 |
| 2021/0259865 A1 | 8/2021 | Holman et al. |

OTHER PUBLICATIONS

"U.S. Appl. No. 17/185,610, Response filed Dec. 11, 2023 to Restriction Requirement mailed Oct. 10, 2023", 7 pgs.

"U.S. Appl. No. 17/185,610, Restriction Requirement mailed Oct. 10, 2023", 8 pgs.

* cited by examiner

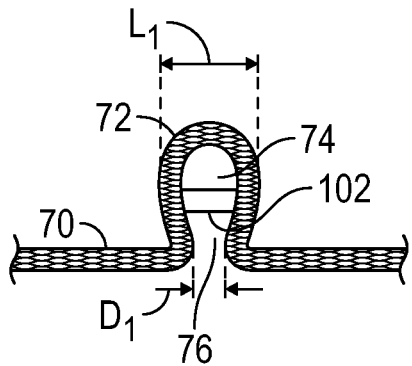
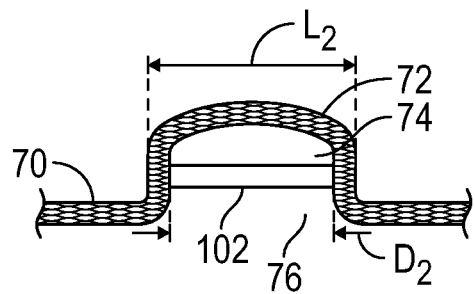
FIG. 27A        FIG. 27B
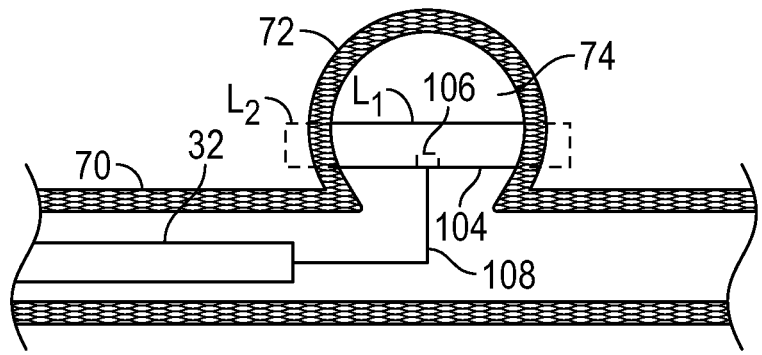
FIG. 28
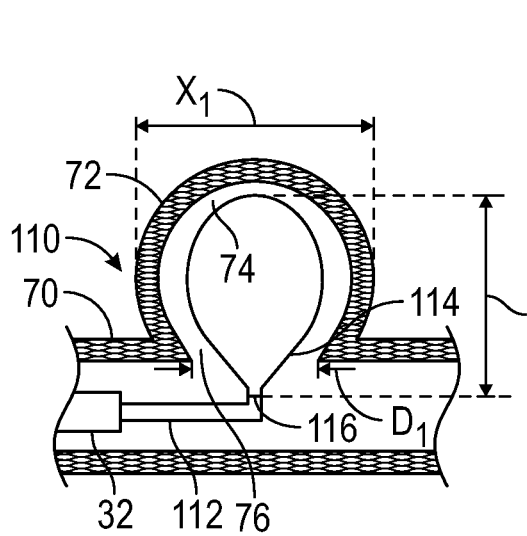
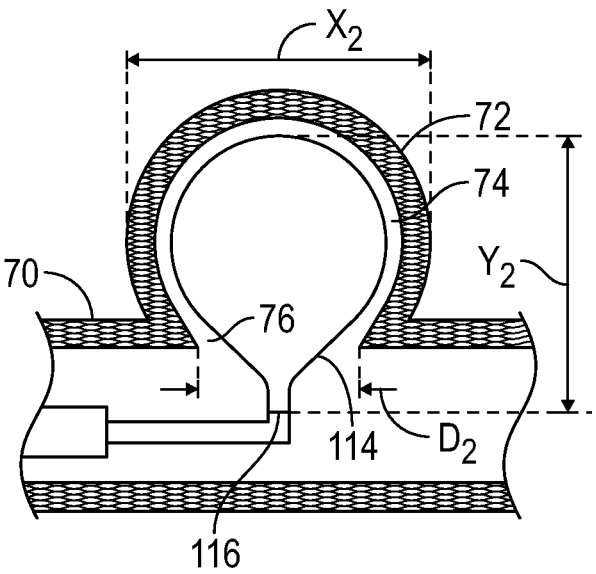
FIG. 29A        FIG. 29B

DEVICES AND METHODS TO TREAT AND PREVENT DIVERTICULITIS

PRIORITY AND RELATED APPLICATIONS

This application claims the benefit of priority to U.S. Provisional Patent Application Ser. No. 63/116,681, titled, "DEVICES AND METHODS TO TREAT AND PREVENT DIVERTICULITIS", filed on Nov. 20, 2020 and to U.S. Provisional Patent Application Ser. No. 62/981,369, titled, "DEVICES AND METHODS TO TREAT AND PREVENT DIVERTICULITIS", filed Feb. 25, 2020, both of which are hereby incorporated by reference in their entirety.

TECHNICAL FIELD

This document pertains generally, but not by way of limitation, to devices and methods that that can be used for treating and preventing diverticulitis.

BACKGROUND

Diverticulitis is caused by infection or inflammation of small pouches in the lining of the colon that bulge outward through weak spots. Such pouches are referred to as diverticula. Each pouch is called a diverticulum and pouches (plural) are called diverticula. Inflammation of the diverticula may lead to bleeding, infections, small tears, perforations, or blockages in the colon.

Diverticular disease results when at least one small pouch in the colon bulges outward through a weak spot. Many Americans over the age 40 have diverticulosis (i.e., the condition of having diverticula), and the condition becomes more common as people age. In many patients, diverticulosis remains asymptomatic. However, in some cases of diverticulosis, the pouches become infected or inflamed. When the pouches become infected or inflamed, the condition is called diverticulitis. This happens in 10 to 25 percent of people with diverticulosis. Most people with diverticulosis do not have any discomfort or symptoms. However, symptoms may include mild cramps, bloating, and constipation. The most common sign is tenderness around the left side of the lower abdomen. If infection is the cause, fever, nausea, vomiting, chills, cramping, and constipation may occur as well. The severity of symptoms depends on the extent of the infection and complications. Diverticulitis can lead to bleeding, infections, perforations or tears, or blockages. These complications always require treatment to prevent them from progressing and causing serious illness.

The infection causing diverticulitis can form an abscess in the colon. An abscess is an infected area with pus that may cause swelling and destroy tissue. Sometimes the infected diverticula may develop small holes, called perforations. These perforations allow pus to leak out of the colon into the abdominal area. If the abscess does not clear up with antibiotics, the doctor may need to drain it. To drain the abscess, the doctor uses a needle and a small tube called a catheter. The doctor inserts the needle through the skin and drains the fluid through the catheter. This procedure is called percutaneous catheter drainage. Sometimes surgery is needed to clean the abscess and, if necessary, remove part of the colon. A large abscess can become a serious problem if the infection leaks out and contaminates areas outside the colon. Infection that spreads into the abdominal cavity is called peritonitis. Peritonitis requires immediate surgery to clean the abdominal cavity and remove the damaged part of the colon. Without surgery, peritonitis can be fatal.

A fistula is an abnormal connection of tissue between two organs or between an organ and the skin. When damaged tissues come into contact with each other during infection, they sometimes stick together. If they heal that way, a fistula forms. When diverticulitis-related infection spreads outside the colon, the colon's tissue may stick to nearby tissues. The organs usually involved are the bladder, small intestine, and skin. The most common type of fistula occurs between the bladder and the colon. It affects men more than women. This type of fistula can result in a severe, long-lasting infection of the urinary tract. The problem can be corrected with surgery to remove the fistula and the affected part of the colon.

The scarring caused by infection may cause partial or total blockage of the large intestine. When this happens, the colon is unable to move bowel contents normally. When the obstruction totally blocks the intestine, emergency surgery is necessary. Partial blockage is not an emergency, so the surgery to correct it can be planned.

Current treatment for diverticulitis focuses on clearing up the infection and inflammation, resting the colon, and preventing or minimizing complications. An attack of diverticulitis without complications may respond to antibiotics within a few days if treated early enough. An acute attack with severe pain or severe infection may require a hospital stay. Most acute cases of diverticulitis are treated with antibiotics (oral or intravenous) and a liquid diet. If attacks are severe or frequent, the doctor may advise surgery. During surgery, the surgeon removes the affected part of the colon and joins the remaining sections. This type of surgery, called colon resection and anastomosis, aims to keep attacks from coming back and to prevent complications. The doctor may also recommend surgery for complications of a fistula or intestinal obstruction. If antibiotics do not correct an attack, emergency surgery may be required. Other reasons for emergency surgery include a large abscess, perforation, peritonitis, or continued bleeding.

Emergency surgery usually involves two operations. The first surgery will clear the infected abdominal cavity and remove part of the colon. Because of infection and sometimes obstruction, it is not safe to rejoin the colon during the first operation. Instead, the surgeon creates a temporary hole, or stoma, in the abdomen. The end of the colon is connected to the hole, a procedure called a colostomy, to allow normal eating and bowel movements. The stool goes into a bag attached to the opening in the abdomen. In the second operation, the surgeon rejoins the ends of the colon. In some instances, rejoining the ends of the colon is not possible and the patient will require the colostomy bag for the rest of their lives.

Currently no reliable way exists to acutely treat diverticulitis, other than supportive measures, or urgent surgery in severe cases. Even for patients in whom symptoms spontaneously resolve (e.g., pain ceases), currently no reliable nonsurgical interventions can be employed to prevent recurrent symptoms. Therefore, a significant unmet medical need remains to develop nonsurgical, minimally invasive interventions that can prevent and treat diverticulitis.

SUMMARY

The present inventors have recognized, among other things, that problems to be solved in treating diverticulitis include the lack of minimally invasive interventions that can treat and prevent diverticulitis. Current treatments include either medication (oral or intravenous) or, in the most extreme cases, surgery. In cases of uncomplicated diverticulitis, such as localized diverticular inflammation, treatment may include antibiotics to treat infections and dietary changes while the bowel heals. In cases of complicated diverticulitis, such as diverticular inflammation associated with an abscess, phlegmon, fistula, obstruction, bleeding, or perforation, treatment may include intravenous antibiotics as well as treatment of other issues such as drainage of an abdominal abscess, if one has formed. However, certain cases the treatment will require surgery. For example, surgery may be required for cases of complicated diverticulitis (such as a bowel abscess, fistula or obstruction, or a perforation in the bowel wall), patients having multiple episodes of uncomplicated diverticulitis, or other considerations (such as a patient with a weakened immune system). Some patients may undergo a reaction and anastomosis, where the surgeon removes diseased segments (resection) of the intestine and then reconnects the healthy segments (anastomosis). If resection is not possible (i.e., there is too much inflammation that it is not possible to rejoin the colon and rectum), the surgeon will perform a colostomy.

The present subject matter can provide solutions to this problem and other problems, such as by providing minimally invasive surgical implants, devices, and methods to treat and prevent diverticulitis and reduce the need that a patient may need to undergo surgery to treat diverticulitis.

In one example, the present subject matter provides devices, systems, and methods to treat diverticulitis. For example, a method of treating diverticulitis can include placing an endoscopic device within a colonic lumen relative to a diverticulum, advancing a delivery shaft from the endoscopic device and into the diverticulum, and releasing a plurality of particles into the diverticulum, wherein the plurality of particles include one or more therapeutic agents to treat the diverticulitis and form a cluster formation to at least partially occlude the diverticulum.

This overview is intended to provide an overview of subject matter of the present patent application. It is not intended to provide an exclusive or exhaustive explanation of the invention. The detailed description is included to provide further information about the present patent application.

BRIEF DESCRIPTION OF DRAWINGS

FIG. 27A illustrates a schematic representation of an expandable ring positioned within a diverticulum in an unexpanded position, in accordance with one example of the present disclosure.

FIG. 27B illustrates a schematic representation of the expandable ring in FIG. 27A in an expanded position.

FIG. 28 illustrates a schematic representation of another expandable ring positioned within the diverticulum, in accordance with one example of the present disclosure.

FIG. 29A illustrates a schematic representation of an inflatable device positioned within the diverticulum, in accordance with one example of the present disclosure.

FIG. 29B illustrates a schematic representation of the inflatable device in FIG. 29A inflated within the diverticulum.

DETAILED DESCRIPTION

Figure 1:
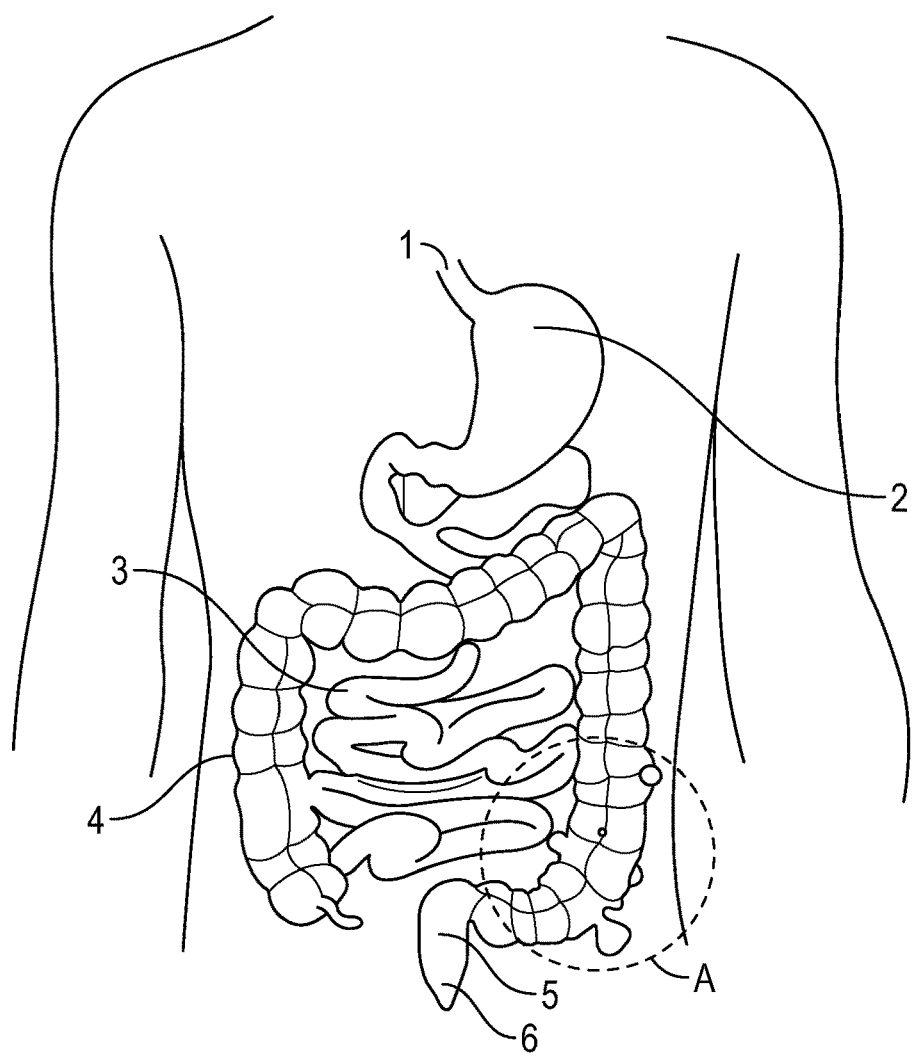
FIG. 1 illustrates a schematic representation of a human digestive tract.

In the following detailed description, reference is made to the accompanying drawings, which form a part hereof. In the drawings, similar symbols typically identify similar components, unless context dictates otherwise. The illustrative examples described in the detailed description, drawings, and claims are not meant to be limiting. Other examples may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Some embodiments described herein generally relate to devices and methods for treating diverticulitis, which is the inflammation or infected diverticula. As used herein, the term "diverticula" and "diverticulum" may refer to a sac- or pouch-like opening from a hollow organ or structure, such as the gastrointestinal (GI) tract, urinary tract, or respiratory tract. Although diverticula can occur in any tubular organ, diverticulosis is of greatest clinical relevance in the lower GI tract (large bowel or colon). Such diverticula may become inflamed or infected, may develop granulomas or may bleed. The devices and methods disclosed herein enable localized treatment of inflamed or infected tissue within the diverticulum.

Figure 2:
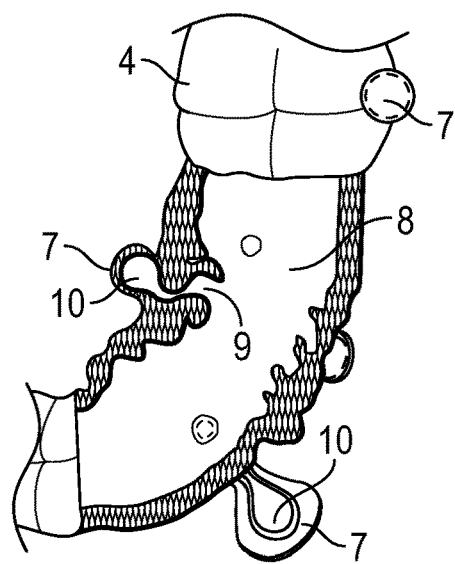
FIG. 2 illustrates a schematic representation of portion "A" in FIG. 1.

FIG. 1 illustrates a schematic representation of a human digestive tract. The digestive tract can be viewed as extending from the mouth, through the throat, down the esophagus 1 into the stomach 2 and to the small intestine 3, proceeding through the colon 4 (large intestine) to the rectum 5 and terminating at the anus 6. FIG. 2 illustrates a close-up view of section "A" in FIG. 1 and shows the presence of diverticula 7 in the colon 4. As seen in FIG. 2, the diverticula 7 are pouch-like structures or projections that extend from or through the walls of the digestive tract, such as at the colon 4. The diverticula 7 extend from a digestive tract lumen 8 (also referred to herein as "colon lumen 8") and define an ostia 9 (the opening) and a cavity 28.

Figure 3:
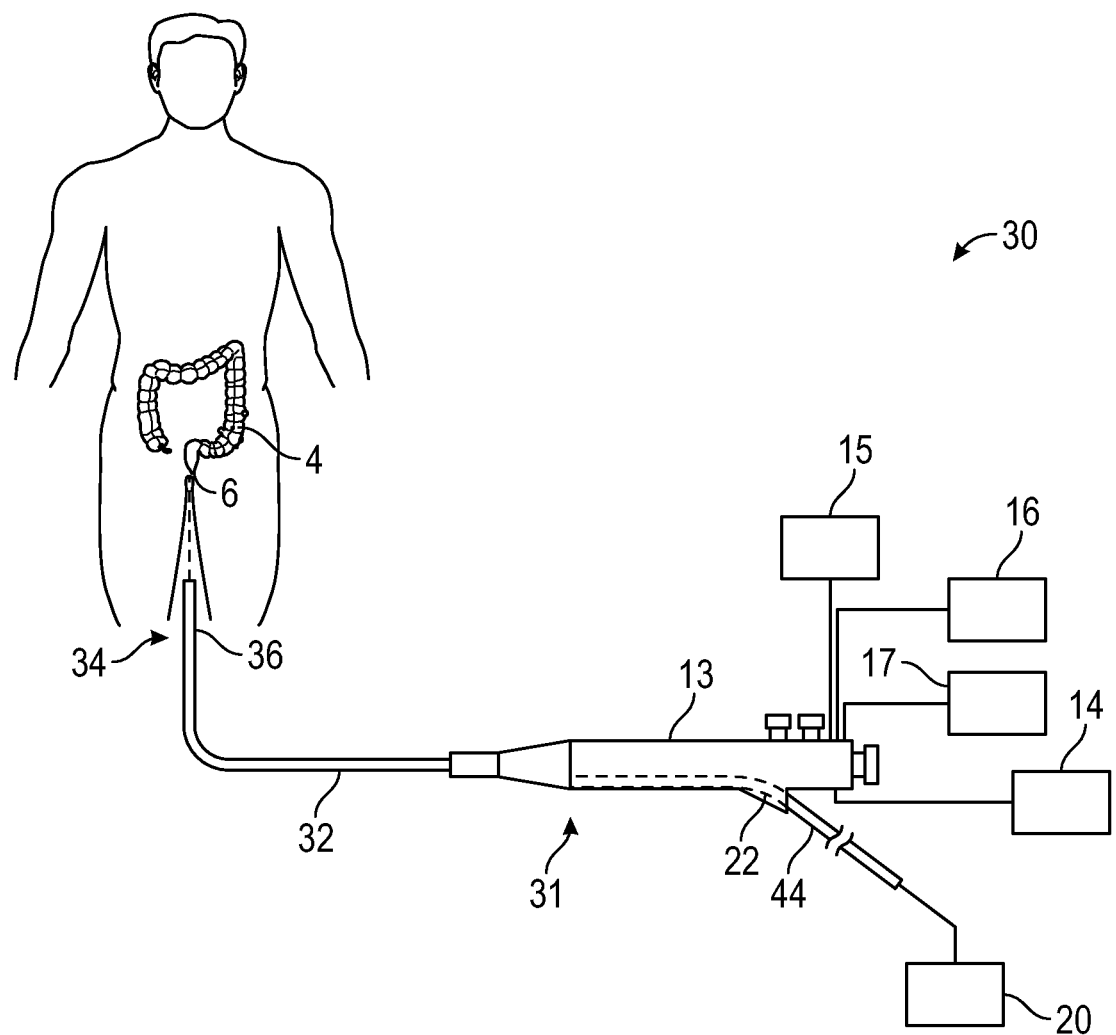
FIG. 3 illustrates a schematic representation of an endoscopic system for treating a diverticulum, in accordance with one example of the present disclosure.
Figure 4:
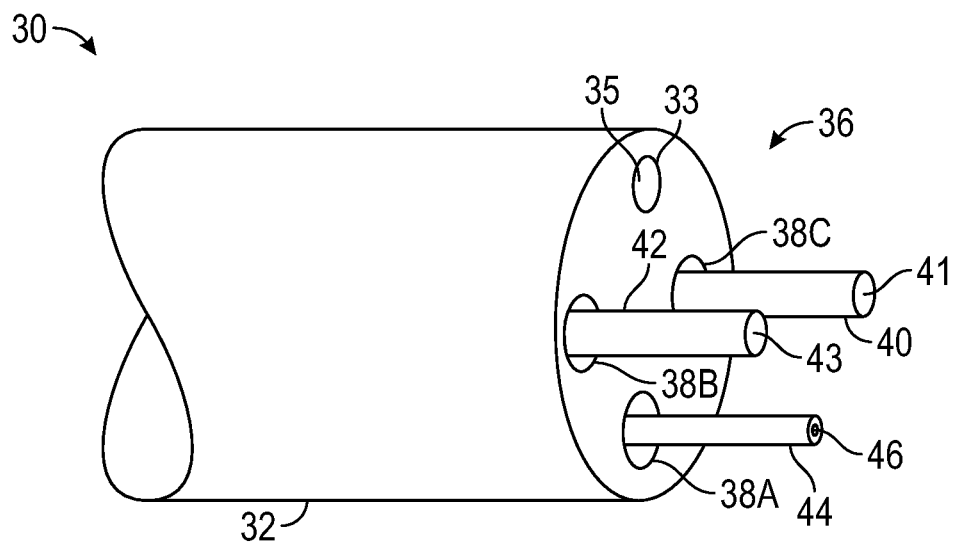
FIG. 4 illustrates a schematic representation of a portion of an endoscopic device for treating diverticulitis, in accordance with one example of the present disclosure.

FIG. 3 illustrates an endoscopy system 30 including an endoscopic device 31 (also referred to herein as "endoscope 31") and FIG. 4 illustrates a perspective view of a working portion 36 of the shaft 32. The endoscopy system 30 of FIG. 3 is an illustrative example of an endoscopy system 30 suitable for use with the systems, devices and methods described herein, such as treatment and prevention of diverticulitis. The endoscopic device 31 can include a main body 13 (e.g., handle) and a shaft 32. The shaft 32 can extend from the main body 13 and have a working portion 36 at a distal end 34 of the shaft 32. The shaft 32 can be semi-rigid or semi-flexible such that manipulation of the shaft 32 within an anatomical structure (e.g., colon, sigmoid colon, descending colon, rectum, colonic lumen, etc.) may easily be facilitated. In on example, shaft 32 can be selectively steered and is configured to be inserted into the color or large intestine of a patient.

In one example, the shaft 32 can be insertable into an anatomical region for imaging and to provide passage of one or more treatment devices for treatment, or one or more therapeutic devices for treatment of a disease state associated with the anatomical region.

In on example, the endoscope 31 can display, on a monitor 15, an image captured by an optical imaging system 33 at the working portion 36 of the shaft 32. Various channels (collectively referred to, hereafter, as simply a "channel") can provide functions for endoscopic examination and treatment, such as air insufflation, irrigation, and treatment tool insertion. The various channels are formed in the shaft 32 along the axial direction thereof. As shown in FIG. 4, the working portion 36 includes a plurality of channels 38A-C disposed coaxially through the shaft 32 to facilitate proximal and/or distal movement of any number of devices 40, 43, 44 therethrough. In this manner, devices 40, 43, 44 may be moved distally through shaft 32 to extend distally from working portion 36 such that devices 40, 43, 44 may be utilized to treat a desired surgical site (e.g., diverticula 7), as discussed in further detail herein. At least one channel is a device channel, e.g., channel 38A, is in communication with an instrument port 22 of the endoscope 31.

In one example, the optically imaging system 33 can also be incorporated into the shaft 32 such that the user can visualize the surgical site. The optically imaging system 33 can include, for example, but not limited to, a camera 35 and a light source 14.

In one example, the device 41 may be a suction device and/or an aspirator configured to remove undesirable materials from diverticula for purposes of treating diverticulitis. For example, device 41 may be used to remove, via suction and/or aspiration, feces and other materials from a diverticulum. With this purpose in mind, device 41 may be operably connected to a suitable suction source or suction pump 16 to facilitate suction of material via a distal end 41 thereof.

In one example, device 42 may be an irrigation or lavage device configured to flush out the cavity of an organ or wound utilizing fluid (e.g., water or an antiseptic agent)

expelled from the device 42. More specifically, the device 42 may be operably connected to a suitable fluid pump 17 to facilitate the expulsion of fluid from a distal end 43 of device 42 for purposes of flushing out undesirable material from a diverticulum.

In one example, the system 30 can include a treatment device that is configured to treat and/or prevent diverticulitis by removing the diverticulum. As discussed herein, the diverticulum can be removed by treating the diverticulum bioactivity of the diverticulum is affected such that the diverticulum will eventually necrose and slough off. In one example, the device 44 is the treatment device configured to deliver treatment materials and/or devices to the diverticulum. The treatment device 44 can be inserted into the endoscope 31 through instrument port 22. The treatment device 44 can be coupled to a variety of devices 20 (delivery sheaths, activators, pumps, suction, etc.) that can be used with the treatment device 44 to treat the diverticulum.

In one example, device 44 is a treatment device configured to delivery treatment materials and/or treatment structures to the diverticula. In one example, device 44 may be a material delivery device to deliver one or more treatment materials into and/or adjacent to a diverticulum for the purpose of treating diverticulitis. In one example, the treatment material includes a plurality of particles. The plurality of particles can include one or more of magnetized particles with anti-microbial or pharmaceutical drug coatings and/or bio-degradable medicated particles, as discussed herein. In an example, the opening 46 of the device 44 can be a flexible opening such that particles having various dimensions can be dispersed. In one example, the flexible opening enables one particle to be dispersed at a time. That is, the opening 46 can have a diameter that retains the plurality of particles within a shaft of the device 44. Thus, an unstretched diameter can be less than a diameter of the plurality of particles. As particles pass through the opening 46, the opening can stretch to allow the particles to pass. Since the opening 46 is formed from an elastic material, a plurality of particles having various diameters can be delivered. In one example, the plurality of particles can be dispersed one at a time. However, other configurations for allowing either one particle or a group of particles to be delivered at once are contemplated.

Prior to treating the diverticulum with the device 44, devices 40, 42 can be used to remove any undesirable material (e.g., feces, pus, bacteria, blood, and/or other infected material) contained within a cavity of the diverticulum. Once the diverticula has been aspirated and/or flushed, the device 44 (also referred to herein as "treatment device") may be utilized to treat the diverticulum. In one example, the device 44 can be inserted through the instrument port 22 of the endoscope 31 for guidance through the channel 38A in the shaft 32 of the endoscope 31 to the diverticulum along the inner lining of the colon 4.

Figure 5:
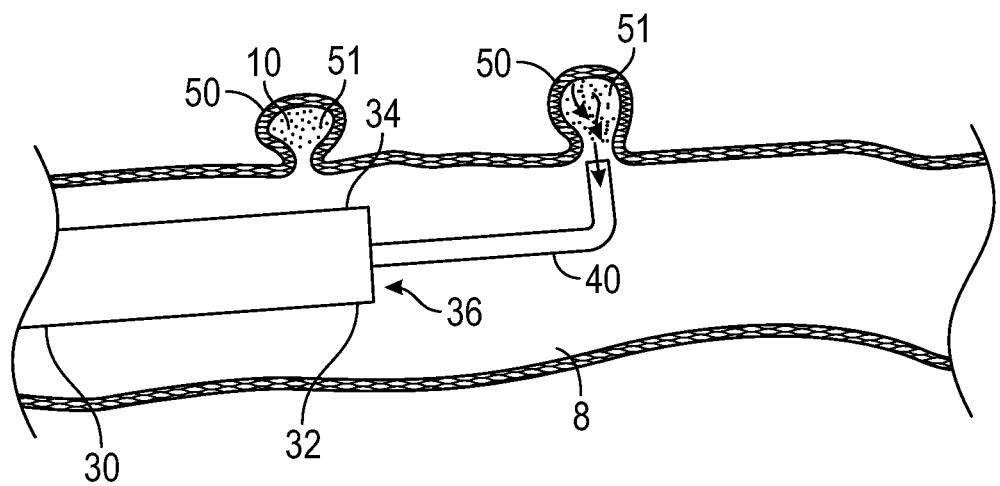
FIG. 5 illustrates a schematic representation of the endoscopic device of FIG. 3 in use to illustrate a method of treating diverticulitis, in accordance with one example of the present disclosure.
Figure 6:
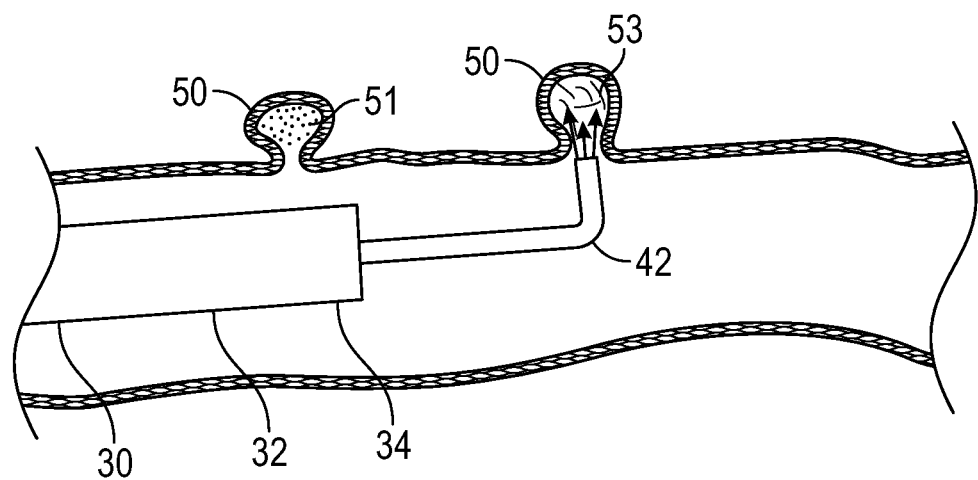
FIG. 6 illustrates a schematic representation of the endoscopic device of FIG. 3 in use to illustrate a method of treating diverticulitis, in accordance with one example of the present disclosure.
Figure 7:
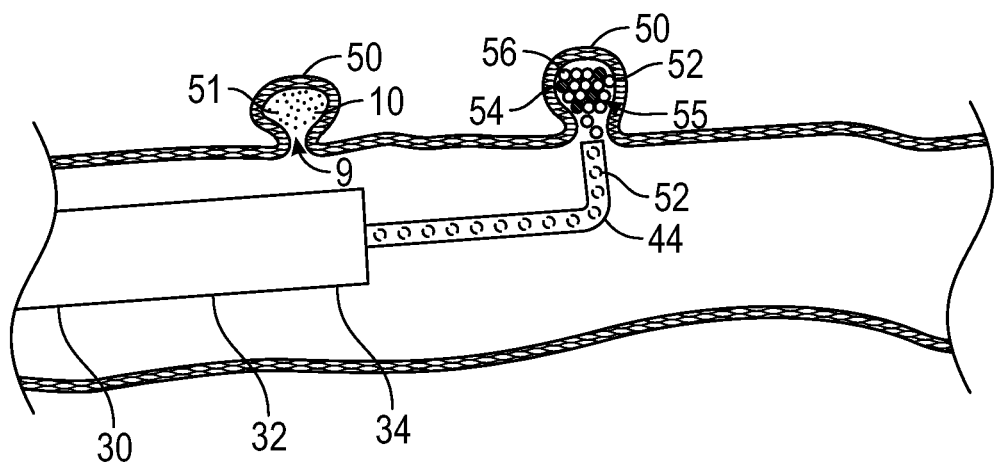
FIG. 7 illustrates a schematic representation of the endoscopic device of FIG. 3 in use to illustrate a method of treating diverticulitis by introducing a plurality of particles into the diverticulum, in accordance with one example of the present disclosure.

FIGS. 5-7 illustrate a method of treating diverticulitis, according to some examples of the present disclosure. For purposes of discussion, the method illustrated by FIGS. 5-7 is shown to include the use of device 30 of FIG. 3 including instruments 40, 41, 44. However, the method illustrated by FIGS. 5-7 and described in detail below, may be employed utilizing any suitable endoscopic device in conjunction with any suitable surgical instruments (e.g., treatment device) for effecting the treatment of diverticulitis detailed below.

Referring to FIG. 5, shaft 32 initially is entered into a colon lumen 8 (e.g., sigmoid colon, descending colon, rectum, etc.) and placed relative to a diverticulum 50 such that the working portion 36 is proximate to a target diverticulum 50. As seen in FIG. 5, the diverticulum 50 includes undesirable material 51 contained within the cavity 10 of the diverticulum 50. In an instance where a patient has diverticulitis, the undesirable material 51 can include feces, pus, bacteria, and/or other infected material. Once appropriately placed, device 40 is utilized to aspirate or suction the diverticulum 50, as illustrated in FIG. 5. For example, device 40 such as an aspirator can be advanced from the distal end 34 of the shaft 32 and is placed proximate to or within the diverticulum 50 and is activated. That is, aspiration and/or suction generated by a suction pump (suction pump 16 in FIG. 1) connected to the device 40 can remove the unwanted material 51 contained within the cavity 10 of the diverticulum 50.

Subsequent to, prior to, or substantially simultaneously to aspirating a diverticulum 50, device 42 may be utilized to lavage or irrigate the diverticulum 50, as depicted by FIG. 6. In one example, device 42 is a lavage device and can be advanced from the distal end 34 and is placed proximate to the target diverticulum 50. The device 42 can then be utilized to "wash out" or flush the diverticulum 50 of any undesirable materials (e.g., feces, blood, etc.) using the pressurized expulsion of fluid (e.g., water, saline, etc.) generated by a suitable fluid pump (fluid pump 17) operably connected to the device 42. In some scenarios, the step of flushing a diverticulum 50 depicted in FIG. 6 may not be necessary, for example, depending on the result of the aspiration step depicted in FIG. 5. Like-wise, in some scenarios, flushing a diverticulum 50 may be performed prior to the step of aspirating the diverticulum 50 and, depending on the result thereof, may render the aspirating step of FIG. 5 unnecessary.

Once the diverticula 50 has been aspirated and/or flushed, as depicted in FIGS. 5 and 6, respectively, device 30 may be utilized to treat the diverticulum 50. In one example, the diverticulum 50 is treated with a plurality of particles 56, as illustrated in FIG. 7. In this example, treatment device 30 is placed proximate to the diverticula 50 and device 44 is utilized to inject a plurality of particles 56 (also referred to herein as "particles 56" and individually as "particle 56") into the diverticulum 50 to treat and prevent diverticulitis. As discussed herein, a portion of the particles 56 can be magnetized such that they adhere (clump) together to form an agglomeration 55 that partially fills (or plugs) the diverticulum 50. The agglomeration 55 of the particles 56 can prevent future fecal entrapment that cause infections that can lead to diverticulitis. The normal colon bio-functionality is not impeded by the introduction of particles 56 and/or the occlusion of the diverticulum 50. The agglomeration 55 that forms from the particles 56 can have a size and/or shape such that the agglomeration 55 is retained within the diverticulum 50.

In one example, the particles 56 can include a plurality of magnetized particles 52 (also referred to herein as "magnetic particles 52") and a plurality of non-magnetic particles 54. As discussed herein, the particles 56 can be introduced into the cavity 10 of the diverticulum 50 in a controlled fashion such that one particle 56 at a time is delivered into the cavity 10. In an example, the device 44 can be positioned adjacent to the ostia 9 or can extend through the ostia 9 and into the cavity 10 of the diverticulum 50 to release the particles 56. In some instances, the ostia 9 of the diverticulum 50 is narrow or even closed due to inflammation and the device 44 can extend through the ostia 9 to deliver and release the particles 56 into the cavity 10 of the diverticulum 50. In an example, the particles 56 should be introduced until the agglomeration 55 is larger than the ostia 9 such that the agglomeration 55 can be retained within the cavity 10 of the diverticulum 50.

Figure 8:
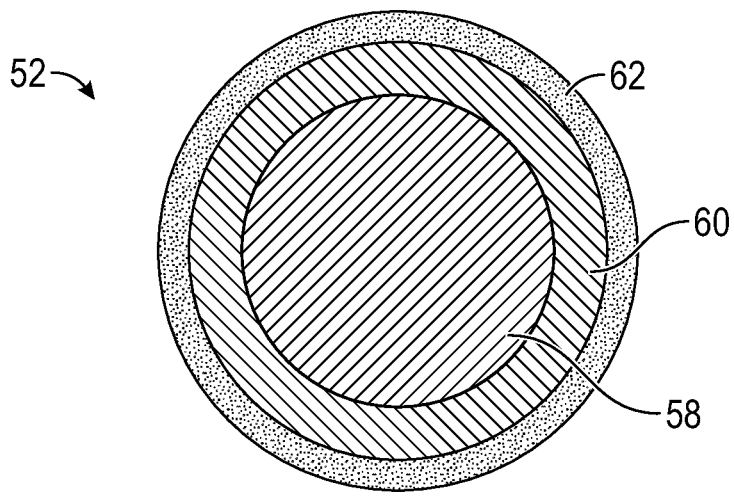
FIG. 8 illustrates an example of a magnetic particle, in accordance with one example of the present disclosure.

FIG. 8 illustrates a cross-section of a magnetic particle 52, according to one example of the present disclosure. The magnetic particle 52 can include a magnetic core 58. The magnetic core can be formed form, but not limited to, a ferromagnetic material such as, iron, cobalt, and their alloys. The magnetic particles 52 can be magnetized such that they are attracted to each other and clump together. In one example, the magnetic particles 52 are magnetized prior to be inserted into the diverticulum 50. In another example, a distal tip of device 44 can be configured to magnetize the particle 52 before the magnetic particle 52 is released from the device 44. An illustrative example of magnetizing is described in U.S. Provisional Application No. 62/984,059, filed on Mar. 2, 2020, and entitled Magnetically Deployable Urinary Stent, which is incorporated by reference herein in its entirety, including for its teaching of magnetizing a device before deployment, which can be used in combination with the plurality of particles of in the present disclosure.

Figure 9:
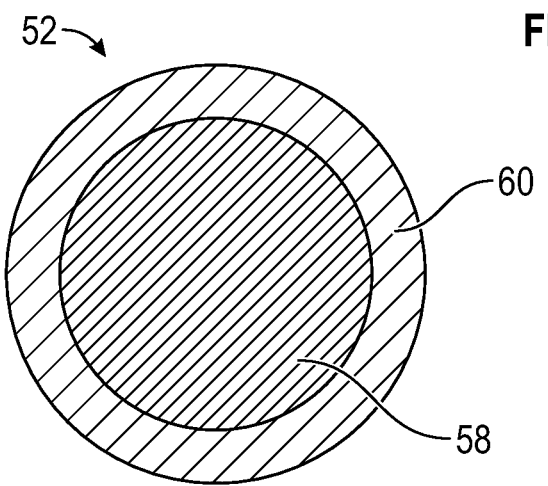
FIG. 9 illustrates an example of a magnetic particle, in accordance with one example of the present disclosure.
Figure 10:
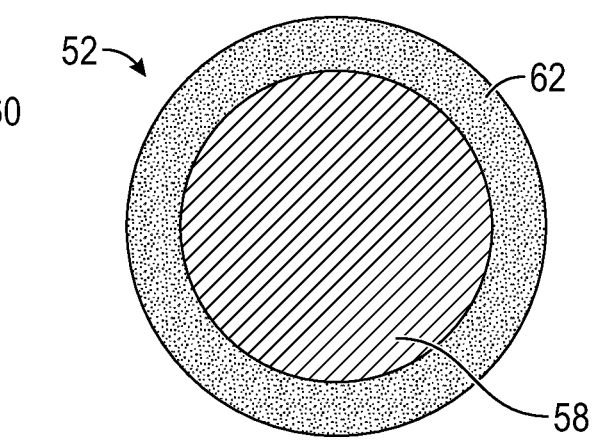
FIG. 10 illustrates an example of a magnetic particle, in accordance with one example of the present disclosure.
Figure 11:
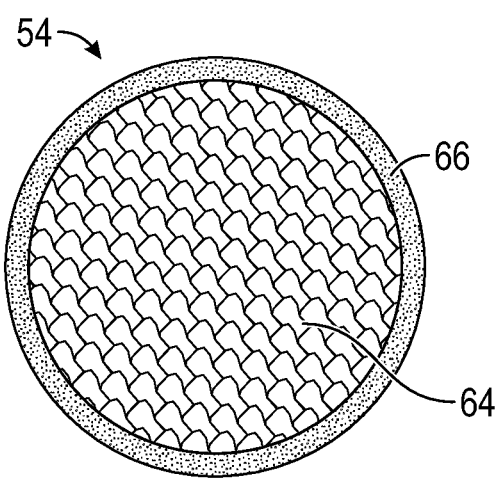
FIG. 11 illustrates an example of a non-magnetic particle, in accordance with one example of the present disclosure.
Figure 12:
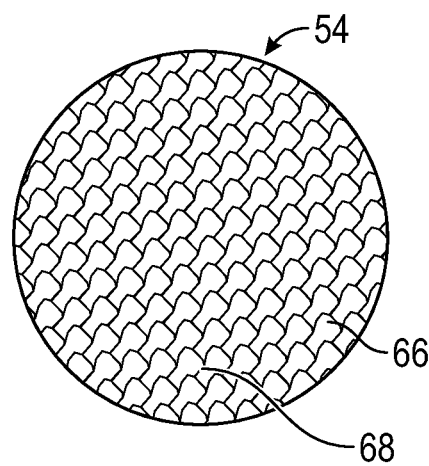
FIG. 12 illustrates an example of a non-magnetic particle, in accordance with one example of the present disclosure.
Figure 13:
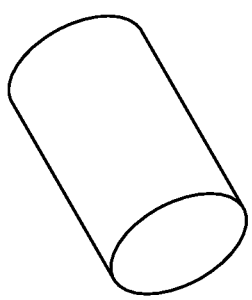
FIG. 13 illustrates an exemplary shape of the plurality of particles, in accordance with one example of the present disclosure.
Figure 14:
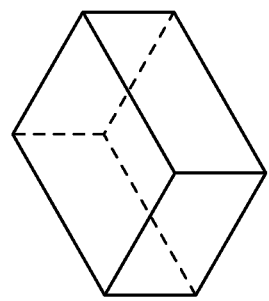
FIG. 14 illustrates an exemplary shape of the plurality of particles, in accordance with one example of the present disclosure.
Figure 15:
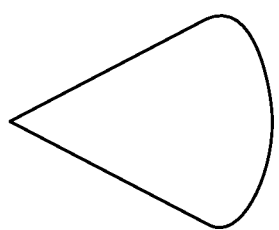
FIG. 15 illustrates an exemplary shape of the plurality of particles, in accordance with one example of the present disclosure.
Figure 16:
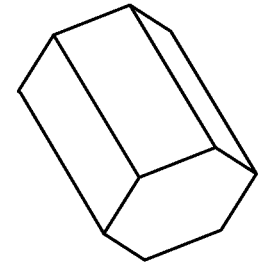
FIG. 16 illustrates an exemplary shape of the plurality of particles, in accordance with one example of the present disclosure.
Figure 17:
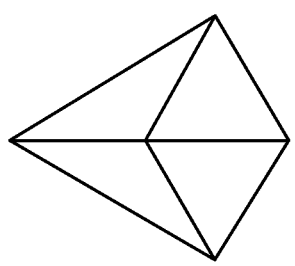
FIG. 17 illustrates an exemplary shape of the plurality of particles, in accordance with one example of the present disclosure.
Figure 18:
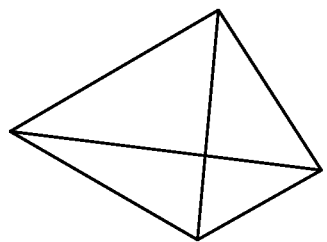
FIG. 18 illustrates an exemplary shape of the plurality of particles, in accordance with one example of the present disclosure.
Figure 19:
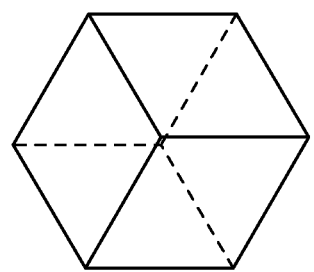
FIG. 19 illustrates an exemplary shape of the plurality of particles, in accordance with one example of the present disclosure.
Figure 20:
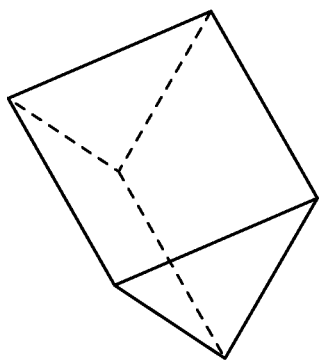
FIG. 20 illustrates an exemplary shape of the plurality of particles, in accordance with one example of the present disclosure.

In one example, the magnetic core 58 can be coated with at least one of an antimicrobial coating 60 and/or a pharmaceutical coating 62 (i.e., medicine) to aid in the healing and prevention of diverticulitis. In one example, one or more of the plurality of magnetic particles 52 can include the magnetic core 58, the antimicrobial coating 60, and the pharmaceutical drug coating 62, as seen in FIG. 8. In one example, one or more of the plurality of magnetic particles 52 can include the magnetic core 58 and the antimicrobial coating 60, as seen in FIG. 9. In one example, one or more of the plurality of magnetic particles 52 can include the magnetic core 58 and the pharmaceutical drug coating 62, as seen in FIG. 10.

In one example, the antimicrobial coating 60 can be selected from any material that inhibits the ability of microorganisms to grow. The antimicrobial coating 60 can promote a long-lasting bactericidal effect without detrimental toxic side effects. In one example, the antimicrobial coating 60 can include at least one of, but not limited to, one or more silver-based antimicrobial agents. Silver-based antimicrobial agents can be selected from, but not limited to, a silver coating and a coating including or formed from silver particles, silver nitrate, silver halide, silver permanganate, silver sulfate, silver nitrite, silver chromate, silver carbonate, silver phosphate, silver (I) oxide, silver sulfide, silver oxide, silver sulfite, a silver thiocyanate, and a silver sulfonamide.

In one example, the antimicrobial coating 60 can include silver. In one example, the silver is non-biodegradable and configured to provide antimicrobial properties as long as the particle is in the diverticulum. For example, the silver can block primary cell metabolism, stop/reduce cellular respiration, and prevent/reduce cell division. In one example, the antimicrobial coating 60 can be biodegradable and be configured to provide a consistent elution of the antimicrobial agents over a period of time. In one example, the antimicrobial coating 60 is a coating of silver. The coating of silver can be a uniform coating to promote antimicrobial properties.

In one example, the pharmaceutical coating 62 is configured to release or elute one or more therapeutic agents, such as an antibiotic, an antimicrobial agent, growth factors, growth inhibitors, an antiseptic agent, an anti-inflammatory agent, an antirestinosis agent, or an antioxidant. The pharmaceutical coating 62 can include a media eluting material. In one example, the pharmaceutical coating 62 can include pores on the surface or other drug storage systems for drug loading. In one example, the media is a drug or therapeutic agent. In one example, the media is one or more antibiotics. In one example, the media is a growth factor. In one example, the media is growth inhibitor. In one example, the media is bacteria to provide for beneficial flora to the digestive tract. In one example, the media is an antimicrobial agent. In one example, the media is delivered over a time-delayed or extended time-release means. In one embodiment an antibiotic is initially released, followed by a time-delayed release of beneficial flora after the antibiotics have dispersed. Suitable media or therapeutic agents include, but are not limited to, an antibiotic agent, beneficial flora, an antimicrobial agent, growth factors, growth inhibitors, an antiseptic agent, an anti-inflammatory agent, an antirestinosis agent, or an antioxidant.

In one example, magnetic particles 52 can include a variety of different magnetic particles 52. That is, the magnetic particles 52 can have different layers and different antimicrobial and/or pharmaceutical coatings. In one example, the magnetic particle 52 includes a magnetic core 58, the antimicrobial layer 60 formed from silver, and a biodegradable pharmaceutical layer 62. In some instances, the target diverticulum 50 may have been infected or inflamed due to diverticulitis. Thus, an initial release of the therapeutic agents contained within the pharmaceutical coating 62 can treat the current infection, inflammation, and other symptoms. Once treated and once the pharmaceutical coating 62 is gone, the antimicrobial layer 60 can continue to provide antimicrobial benefits while the particles occlude the diverticulum; thereby, reducing the risk of reinfection.

As discussed herein, various sizes of the particles 56 can be used. In one example, the particles 56 can have a diameter of about 5 millimeters (mm) or less. However, particles 56 having a diameter larger than 5 mm can be used as well. The size of the particles 56 can be chosen such that voids are minimized while the diverticulum is densely packed.

In addition to the magnetic particles 52, the particles 56 can include non-magnetic particles 54. In one example, the non-magnetic particles 54 can be biodegradable. In another example, the non-magnetic particles are not biodegradable. The non-magnetic particles 54 can be medicated particles that can be inserted into the diverticulum to increase healing and/or to prevent infection of the diverticulum 50. That is, the non-magnetic particles 54 can be drug-eluting particles (e.g., polymer particles—biodegradable or not) that can be placed into the diverticulum 50 to treat diverticulitis.

In one example, the non-magnetic particles 54 can be formed of the materials described for the pharmaceutical coating 62 of the magnetic particles 52. However, in one example, the non-magnetic particles 54 can include a core 64 and a pharmaceutical coating 66. Pharmaceutical coating 66 can be the same as pharmaceutical coating 62. Instead of having a pharmaceutical coating, the entire non-magnetic particle 54 can be formed from the materials disclosed for the pharmaceutical coating 62. That is, the non-magnetic particle 54 can include the biodegradable media including one or more therapeutic agents configured to elute over time. However, one consideration is that as the biodegradable particles 54 degrades, the shape and structure of the agglomeration 55 (see FIG. 7 may change). In one example, the number of biodegradable particles used can be determined such that after the particles degrade, the agglomeration of particles can still be retained within and at least partially occlude the diverticulum.

As seen in FIG. 7, the plurality of particles 56 include both the magnetic particles 52 and the non-magnetic particles 54. To treat a diverticulum that has diverticulitis, the magnetic and non-magnetic particles 52, 54 can be inserted into the diverticulum. The non-magnetic particles 54 (including the therapeutic agents to treat diverticulitis) and the, if included, pharmaceutical coating 62 on the magnetic particle 52 can be used to treat the current infection or other current symptoms of the diverticulitis. In one example, after a time period, a portion of the non-magnetic particles 54 such as the pharmaceutical coating 62 can biodegrade and the magnetic particles 52 including the antimicrobial agent layer 60 and uncoated non-magnetic particles 54 will remain.

If the non-magnetic particles 54 are configured to fully degrade, a number of magnetic particles 52 used can be greater than a number of non-magnetic particles 54 such that once the non-magnetic particles biodegrade, the magnetic particles 52 still form a structure that can be retained within the diverticulum. The antimicrobial properties along with the plurality of particles 56 at least partially occluding the diverticulum, can minimize the risk of a reoccurrence of the diverticulitis. While the biodegradable portions will degrade over time, the magnetic particles 52 can remain within the diverticulum for an extended period of time and if needed, can be removed by multiple methods. For example, the magnetic particles 52 can be removed via aspiration or suction, among others.

As seen in FIGS. 7-12, the particles 56 can generally have the shape of a sphere. However, other shapes are contemplated. Various shapes of the particles 56 are shown in FIGS. 13-20. For example, the particles 56 can have shapes including, but not limited to, a cylinder (shown in FIG. 13), a cuboid (shown in FIG. 14), a cone (shown in FIG. 15), prisms such as hexagonal prism (shown in FIG. 16), a triangular prism (see FIG. 20), a pentagonal prism, and a quadrangular prism, pyramids such as a rectangular pyramid (see FIG. 17), a triangular pyramid (see FIG. 17), and a cube (see FIG. 19). As discussed herein, having particles 56 having different shapes can assist in forming predetermined cluster formations within the diverticulum such that the plurality of particles 56 have a shape and size that can be retained within the diverticulum. That is, by selectively magnetizing a particular shaped particle in a particular manner allows the user to predetermine the shape the particles 56 will assume once the particles are delivered to the diverticulum. In one example, the plurality of particles 56 have the same shape. In one example, the plurality of particles 56 can include more than one shape.

The size of the particles 56 can also vary. For example, the particles 56 can have a maximum dimension within a range of about 5 (mm) or less. The size of the diverticulum can also vary. For example, diverticulum can have dimensions (length and width) of about 5 mm to about 10 mm. The size and shape of the diverticulum being treated can determine the size and shape of the particles being used in the procedure.

Figure 21:
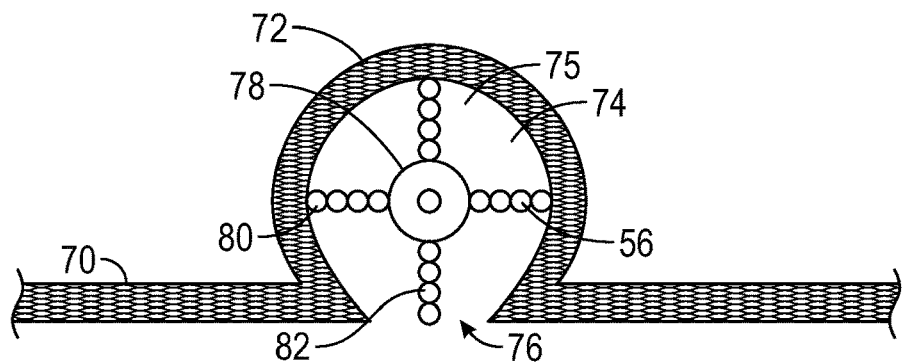
FIG. 21 illustrates a schematic representation of a plurality of particles positioned within a diverticulum, in accordance with one example of the present disclosure.
Figure 22:
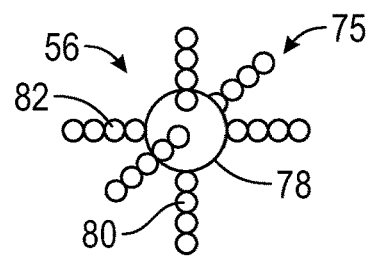
FIG. 22 illustrates a perspective view of the plurality of particles in FIG. 21.

FIG. 21 illustrates a schematic representation of a portion of a colon 70 including a diverticulum 72 being treated. As seen in FIG. 21, the plurality of particles 56 have been introduced into the cavity 74 of the diverticulum 72. The particles 56 can include a main particle 78 that has been selectively magnetized such that smaller particles 80, when introduced into the cavity 74, will attach to the main particle 78 in predetermined locations. As illustrated, the main particle 78 has been magnetized such that as the smaller particles 80 are introduced, arms 82 (or projections) form extending from the main particle 78 at the predetermined locations. The predetermined cluster formation 75 of particles 56 can assist in retaining the particles 56 within the diverticulum 72. In an example, the predetermined cluster formation 75 can have a size greater than a maximum dimension of the ostia 76. FIG. 22 illustrates a perspective view of the predetermined cluster formation 75 in FIG. 20. As seen in FIG. 22, the main particle 78 has a diameter greater than the other particles 80 that form the arms 82. While shown as the main particle 78 centrally located within the diverticulum 72, the main particle 78 can contact an inner surface of the diverticulum 72. In one example, the main particle 78 can be coated with a bioadhesive such that the main particle can attach to the diverticulum 72 prior to introducing the smaller particles 80. Thus, the bioadhesive can be used to further assist the particles to be retained within the diverticulum 72 as the main particle 78 is attached/secured to an inner surface of the diverticulum 72 and the smaller particles 80 are magnetically attached to the main particle 78. While shown as being larger than smaller particles 80, the main particle 78 and the other particles 80 can be the same shape and size or have any size and shape that enables the predetermined cluster formation 75 from being retained and at least partially occlude the diverticulum 72. In one example, the bioadhesive can be selected from, but not limited to, tragacanth, Sodium alginate, Karaya gum, Guar gum, Xanthan gum, Soluble starch, Gelatin, Pectin, Chitosan, among others, etc. In general, any bioadhesive can be used that can promote mucoadhesion.

Figure 23:
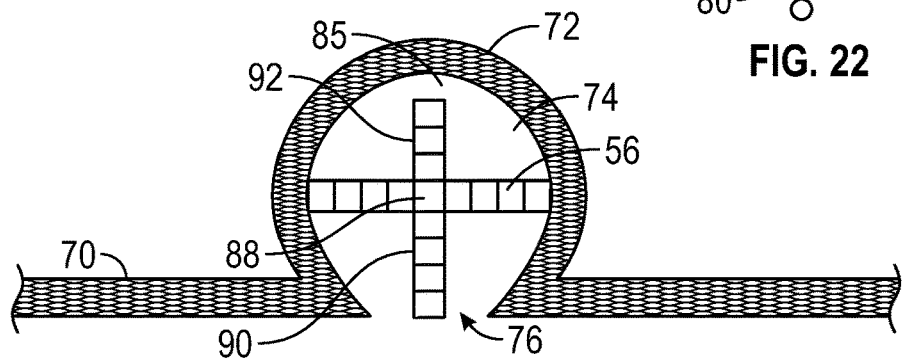
FIG. 23 illustrates a schematic representation of a plurality of particles positioned within a diverticulum, in accordance with one example of the present disclosure.
Figure 24:
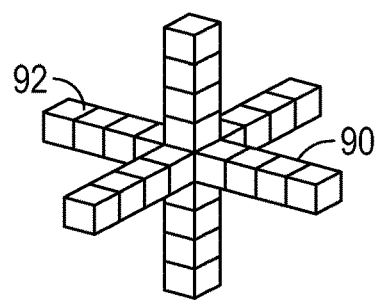
FIG. 24 illustrates a perspective view of the plurality of particles in FIG. 23.

FIG. 23 illustrates a schematic representation of a portion of the colon 70 including the diverticulum 72 being treated. In this example, the plurality of particles 56 include cube shaped particles that have been magnetized such that the predetermined cluster formation 85 is shaped like a plus sign. FIG. 24 illustrates a perspective view of the predetermined cluster formation 85 of FIG. 23. Referring to FIGS. 23 and 24, the predetermined cluster formation 85 includes a central particle 88 and particles 90 adhere together such that arms 92 extend from the central particle 88. In an example, the particles 56 shown in FIGS. 23 and 24 generally have the same shape and size.

As discussed herein, the selective magnetization of the particles 56 such that a predetermined cluster formation can be created assists in retaining the particles 56 within the diverticulum. The shape, size, predetermined cluster formation, and magnetization of particles can be based on a variety of factors.

Figure 25:
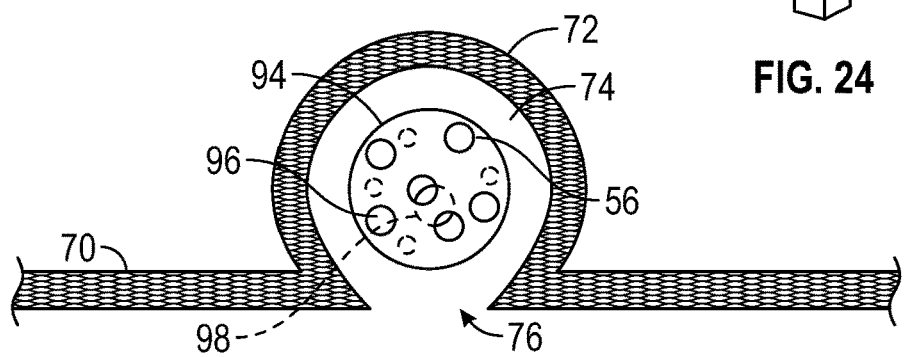
FIG. 25 illustrates a schematic representation of a plurality of particles positioned within a diverticulum, in accordance with one example of the present disclosure.

FIG. 25 illustrates a schematic representation of a portion of a colon 70 including a diverticulum 72 being treated. In the example shown in FIG. 25, an anchor particle 94 has been introduced into the cavity 74 of the diverticulum 72. The size of the anchor particle 94 can be larger than the size of the ostia 76. Thus, a slight dilation of the ostia 76 may occur during or prior to insertion of the anchor particle 94. The anchor particle 94 can be a sphere, an ovoid or other shape. In one example, the anchor particle 94 can include openings 96. The anchor particle 94 can be magnetized and/or the interior of the anchor particle 94 can include a magnetic core 98. In one example, an exterior surface of the anchor particle 94 can include a bioadhesive such that anchor particle 94 can be inserted and coupled to an inner surface of the diverticulum 72.

Additionally, the anchor particle 94 can be loaded with a plurality of particles 56 (magnetic and non-magnetic particles), as described herein. That is, the anchor particle 94 can be inserted into the diverticulum with the particles 56 already positioned within the interior of the anchor particle 94. In one example, the anchor particle 94 is first positioned within the diverticulum 72, and the particles 56 are subsequently introduced into and/or around the anchor particle 94. In one example, the anchor particle 94 is formed form or includes silver. The anchor particle 94 including the plurality of particles 56 can initially treat the diverticulitis and at least partially occlude the diverticulum 72 to prevent a reoccurrence of the diverticulitis.

In one example, if a reoccurrence of the diverticulitis occurs, a patient can go in for the minimally invasive treatment of introducing additional particles 56 into the anchor particle 94. For example, non-magnetic particles including a therapeutic agent can be introduced and/or magnetized particles including a pharmaceutical layer can be introduced via an endoscopic procedure, as discussed herein.

Figure 26:
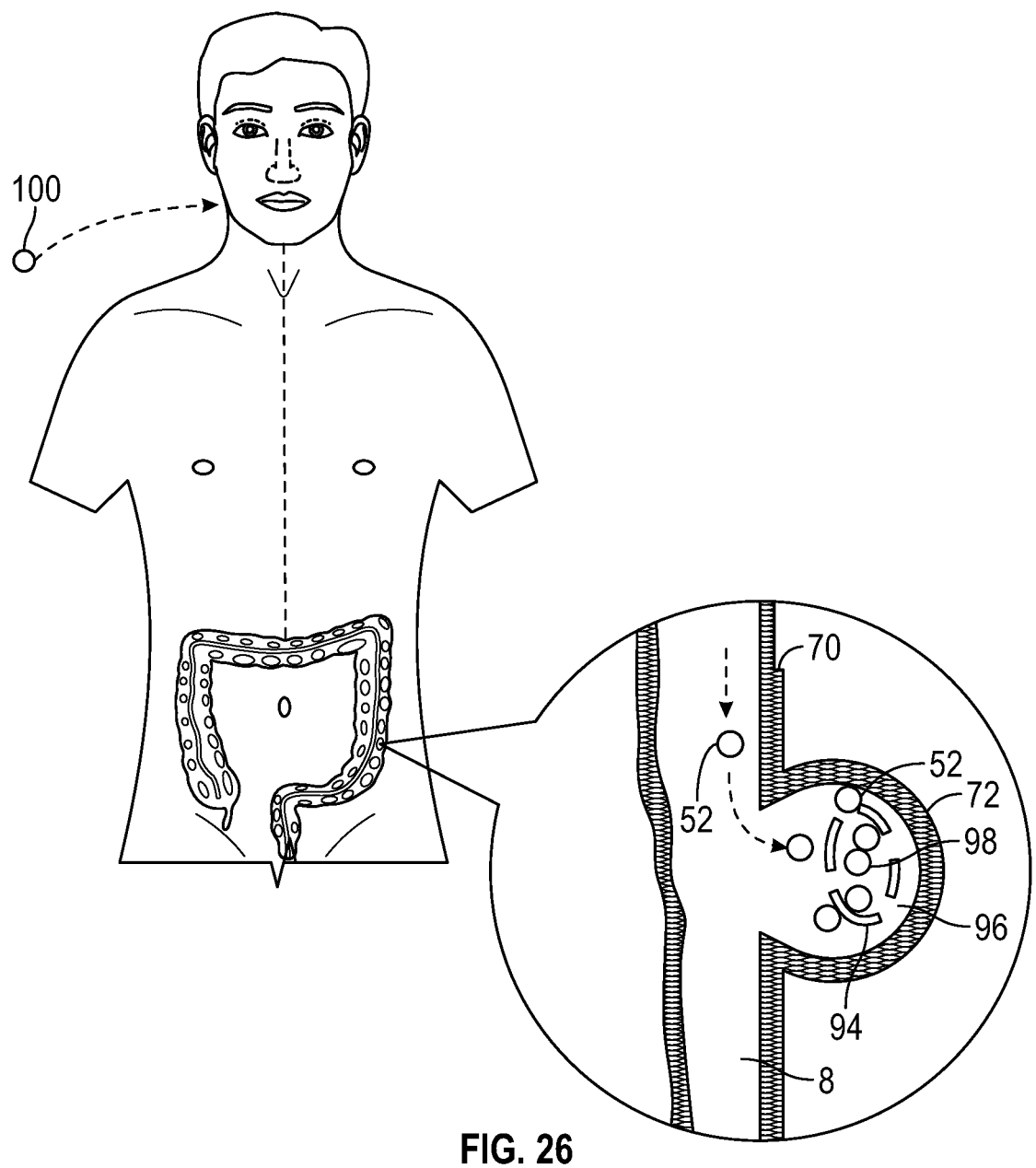
FIG. 26 illustrates the movement of a plurality of magnetic particles ingested by a patient in pill form, in accordance with one example of the present disclosure.

In one example, instead of having the minimally invasive procedure to reintroduce particles 56 into the diverticulum 72 and into the anchor particle 94, FIG. 26 illustrates another method of treating the patient. The patient in FIG. 26 has already had the anchor particle 94 introduced into the diverticulum 72. The anchor particle 94 can be magnetized and/or includes a magnetic core 98. The patient can take a pill 100 including a plurality of magnetized particles 56 that includes one or more therapeutic agents, as discussed herein. As the pill breaks down, the plurality of magnetized particles 52 will make their way to the colon 70. The magnetic force of the anchor particle 94 and/or magnetic core 98 can attract at least some of the magnetized particles 52 as they pass by the diverticulum 72, thus providing treatment. Therefore, the anchor particle 94 acts like a beacon for magnetized particles that are introduced into the body, e.g., via the pill 100 or otherwise. The magnetized particles 52 can adhere to the anchor particle 94 itself (if the anchor particle 94 is magnetic) or enter the anchor particle 94 via the openings 96 and adhere to the magnetic core 98. Therefore, in one example, the patient can take the pill 100 containing the magnetized particles 52 at the onset of minor symptoms to proactively treat diverticulitis before more serious complications occur.

As discussed herein, fecal or other material can become trapped within diverticulum and become infected. Once matter enters a diverticulum, one cause for remaining trapped can be the size of the ostia (the opening of the diverticulum). FIGS. 27-31 illustrate examples of devices and methods for expanding the ostia and/or reducing the height of the diverticulum. The examples shown can alter the shape of the diverticulum such that the risk of material becoming lodged and trapped within the diverticulum is reduced, thereby reducing the risk of infection.

FIG. 27A illustrates a schematic diagram of a colon 70 including a diverticulum 72. As seen in FIG. 27A, an expandable ring 102 (also referred to herein as "ring 102") can been inserted into the cavity 74 of the diverticulum 72. The ring 102 can have a first length "L1" and the ostia 76 can have a first diameter "D1". In FIG. 27B, the expanding ring 102 has expanded from the first length "L1" to a second length "L2" such that the ostia 76 has a second diameter "D2" that is greater than the first diameter "D1". By increasing the diameter of the ostia 76, the diverticulum is shallowed and can make it difficult for infection to inflame the ostia and block air flow into and out of the diverticulum. Thus, the risk of infection can be reduced.

In one example, the expandable ring 102 can be a self-expanding ring formed form a shape memory material, e.g., nitinol. In one example, the ring 102 can be any biocompatible, latex-free, polymer. In one example, the ring 102 can be a silicone elastomer. In one example, the ring 102 is non-biodegradable and the ring 102 can remain within the diverticulum 72. By increasing the ostia 76 diameter and shallowing the depth of the diverticulum 72, the risk of fecal or other material getting trapped and infected can be reduced.

In one example, the ring 102 can be biodegradable. In that instance, the ring 102 can be used for a predetermined time to stretch-out the ostia 76 such that once the ring 102 degrades, the ostia 76 diameter remains closer to the second diameter "D2". In some examples, the ring 102 can include one or more therapeutic agents that can assist in treating or preventing diverticulitis while the ring 102 is positioned within the diverticulum 72. In on example, the ring 102 can be magnetized and the particles, as discussed, herein can be introduced and couple magnetically to the ring 102.

FIG. 28 illustrates another example of an expanding ring 104 used to open and/or stretch-out the ostia 76. In this example, the ring 104 includes a ratcheting or similar mechanism for expanding. The ring 104 can be inserted and positioned into the diverticulum 70 having a first length "L1". A tool 108, extending from the shaft 30, can engage a mechanism 106 on the ring 104 and actuate the ring 104 to expand to a second length "L2". The ring 104 can be formed of the same materials as discussed for ring 102 in FIGS. 27A and 27B.

FIGS. 29A and 29B illustrate another example of opening and/or stretching-out the ostia 76. In this example, the device 110 can include a flexible conduit 112 and a balloon-forming chamber 114 that are translatable within the shaft 30. The flexible conduit 112 and the balloon-forming chamber 114 can be positioned within a passageway, e.g., channel 38A (shown in FIG. 4). The flexible conduit 112 can have a hollow interior portion for conveying air or other fluids.

The balloon-forming chamber 114 can be positioned at an end of the flexible conduit 112 For example, the balloon-forming chamber 114 can be positioned on a portion of the flexible conduit 112. The balloon-forming chamber 114 can be, for example, a flexible, inflatable bladder formed from an elastic material. The balloon-forming chamber 114 can be attached or fused to the flexible conduit 112 at an attachment point 116 or may integrally be formed with the flexible conduit 112 such that the balloon-forming chamber 114 and the flexible conduit 112 form a unitary structure.

The flexible conduit 112 and the balloon-forming chamber 114 can be formed from a material that exhibits elasticity and biocompatibility. As a non-limiting example, the flexible conduit 112 and the balloon-forming chamber 116 can be formed from a silicone-containing material, such as silicone rubber, or from a fluoro-rubber. As another non-limiting example, the flexible conduit 112 and the balloon-forming chamber 114 can be formed from polymer material or a thermoplastic material having a high elasticity.

FIG. 29A illustrates the balloon-forming chamber 114 positioned within a cavity 74 of the diverticulum 72. A size of the balloon may be freely variable to conform to a shape of the diverticulum 72. The balloon-forming chamber 114 can have an unexpanded state and an expanded state. A fluid, such as air or saline, may be introduced into the balloon-forming chamber 114 through the flexible conduit 112. As the fluid is introduced into the balloon-forming chamber 114, the balloon-forming chamber 114 can transition from the unexpanded state to an expanded state as a wall of the balloon-forming chamber 114 expands outward. The fluid may be introduced into the balloon-forming chamber 114 until at the wall of the balloon-forming chamber 114 contacts an inner surface of the diverticulum 72. For example, the balloon-forming chamber 114 can be initially expanded by filling the balloon-forming chamber 114 with the fluid such that at least a portion of the balloon-forming chamber 114 substantially fills the diverticulum 72.

A user, using an optically imaging system, can determine how much fluid to introduce into the balloon-forming chamber 106 such that the ostia 76 is sufficiently opened. For example, as seen in FIG. 29A, the balloon-forming chamber 106 is partially filled, and the ostia 76 has a first diameter "D1". Depending on the dimensions of the balloon-forming chamber 106 and the diverticulum 70, the amount of fluid and expansion needed will vary between each diverticulum that is treated. As seen in FIG. 29B, the ostia 76 can been expanded such that the ostia 76 has a second diameter "D2" that is larger than the first diameter "D1". The balloon-forming chamber 114 have a first dimension "X1" in a first direction and a second dimension "Y1" in a second direction, the second direction substantially perpendicular to the first direction. The balloon-forming chamber 114 can have a predetermined expansion ration such that the first dimension "X1" and the second dimension "Y1" based on the amount of fluid introduced is known and the expansion of the ostia 76 can be controlled. After a certain amount of time, the balloon-forming chamber 114 can be deflated and the device 110 can be removed.

While the rings 102, 104 discussed herein with respect to FIGS. 27 and 28 can remain in place to maintain the expansion of the ostia, the balloon-forming chamber 114 can be removed. In on example, the expansion of the ostia takes into account the recoil of tissue. That is, the ostia is expanded such that dimensions of the ostia after recoil fits within certain parameters. These parameters can be determined clinically or may be stored in a lookup table to determine the necessary dimensions of an ostia to prevent fecal entrapment.

Figure 30:
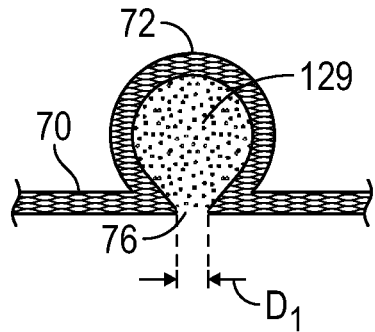
FIG. 30 illustrates a schematic representation of a diverticulum that includes unwanted material, in accordance with one example of the present disclosure.
Figure 31:
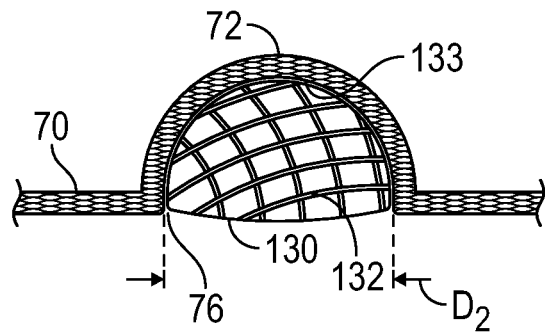
FIG. 31 illustrates a schematic representation of a stent positioned within the diverticulum shown in FIG. 30, in accordance with one example of the present disclosure.

FIG. 30 illustrates a portion of the colon 70 including a diverticulum 72 including entrapped material 129. The ostia 76 of the diverticulum 72 has a first dimension "D1" that is preventing the entrapped material 129 from exiting the diverticulum 72. FIG. 31 illustrates a stent 130 that can be positioned within the diverticulum 72 to expand the ostia 76 to a second dimension "D2". The second dimension "D2" is sufficient such that material does not become entrapped. In one example, the stent 130 can be a self-expanding stent. In one example, the stent 130 can include a biocompatible adhesive 132 such that the stent 130 is secured to the inner surface 133 of the diverticulum 72. The stent 130 can be formed of biocompatible materials. In one example, the stent 130 can include any materials included in coatings 60, 62, and 66. The stent 130 can be a drug eluting stent or have a coating that has one or more eluting therapeutics. In one example, a portion of the stent 130 can include silver to provide antimicrobial properties to the stent to further reduce infection.

In one example, the stent 130 or a portion of the stent can be magnetic such that a plurality of magnetic particles (as shown in FIGS. 8-10) can be introduced and couple to the stent 130. That is, a plurality of magnetic particles including any of the coatings 60, 62, 66 discussed herein can be introduced and couple to the stent 130 to prevent infection.

In additional to expanding the ostia 76, the stent 130 can act as a support structure to maintain the integrity of the diverticulum 72 and prevent or minimize the risk of rupture.

Figure 32A:
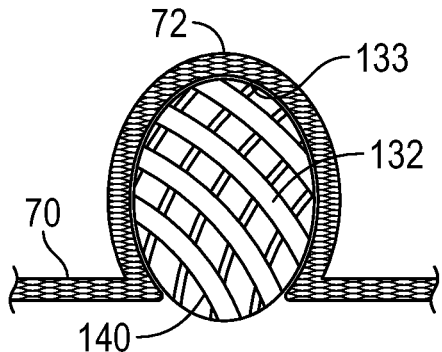
FIG. 32A illustrates a schematic representation of a collapsible stent positioned within the diverticulum, in accordance with one example of the present disclosure.
Figure 32B:
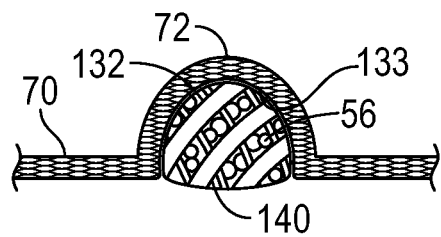
FIG. 32B illustrates a schematic representation of the collapsible stent in FIG. 32A in a collapsed state including a plurality of particles, in accordance with one example of the present disclosure.

While the stent 130 in FIG. 31 expanded the ostia 76 and diverticulum 72, the stent 140 in FIGS. 32A and B reduce the size of the diverticulum 72. As discussed herein, some diverticulum 72 can be stretched thin and extra pressure put on the diverticulum 72 through material or gas can cause the patient pain. Thus, the stent 140 can be a collapsible stent to support and reduce the stretching and pressure put on the diverticulum 72. For example, the stent 140 can include the biocompatible adhesive and initially expands such that the inner surface 133 of the diverticulum 72 contacts the stent 140 and the stent 140 adheres to the inner surface 133 of the diverticulum 72. Other adherence mechanisms are contemplated, such as fusing via electrical energy, sutures, etc., to adhere the stent 140 to the diverticulum 70. Once adhered, the stent 140 can collapse, as seen in FIG. 32B. Since the inner surface 133 is adhered to the stent 140, any pressure that would normally stretch the diverticulum 70 is eliminated (or drastically reduced) thereby reducing the pain felt by the patient. By reducing the size of the diverticulum 72 the risk of infection can be reduced. As discussed herein with stent 130, stent 140 can be magnetic and be used with the plurality of particles as discussed herein.

In one example, prior to, simultaneously, or after the stent 140 is reduced, at least one particle 56 (magnetic and/or non-magnetic) can be introduced into the stent 140. In one example, the shape of the collapsed state of the stent 140 can be such that the stent 140 can collapse around the at least one particle 56 or an agglomeration of a plurality of particles 56. For example, the particles 56 can be retained within the stent 140 because of the shape of the stent 140 in the collapsed state and thus the stent 140 and the at least one particle 56 do not necessarily need to be magnetic. That is, a maximum dimension of the opening of the collapsed stent 140 is less than a minimum dimension of the agglomeration of particles 56 or a diameter of the at least one particle 56. In one example, the stent 140 can be magnetic and can receive at least one magnetic particles 52 and, optionally, as least one non-magnetic particle 54.

As illustrated in FIG. 32B, a plurality of particles 56 are retained within the stent 140 and thus within the diverticulum. However, as discussed, at least one larger particle 56 could be used such that the space defined by stent 140 is filled with the at least one particle 56 further occluding the diverticulum 72 and preventing further infection. The example shown in FIGS. 32A and B support the diverticulum, as well as prevent reinfection by at least partially occluding the diverticulum.

Figure 33:
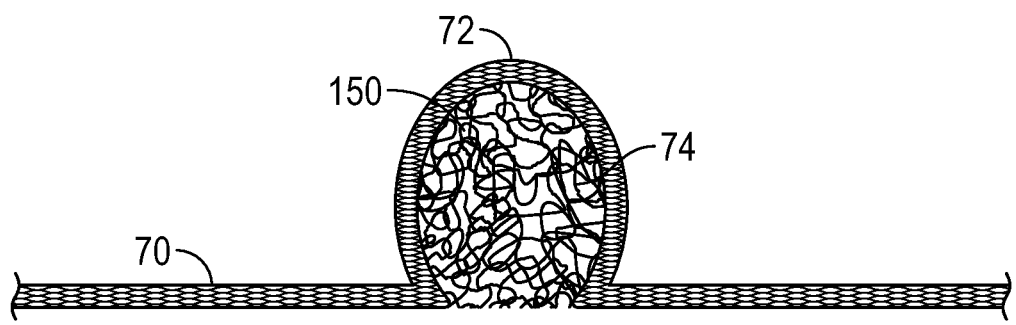
FIG. 33 illustrates a schematic representation of the diverticulum filled with an occluding material, in accordance with one example of the present disclosure.

Referring now to FIG. 33, a method of preventing the recurrence of diverticulitis according to another examples includes occluding the diverticulum 72 by injecting an occluding material into the cavity 74 of the diverticulum 72 is shown. The occluding material 150 is configured to substantially solidify such that the occluding material remains within the diverticulum 72; thereby, preventing any further occurrences of material becoming entrapped within the diverticulum. For example, undesirable material is prevented from entering the already-occupied diverticulum 72. The occluding material 150 can be selected from, but not limited to, a biocompatible adhesive, mucosal adhesives, superglue (cyanoacrylate—e.g., ethyl, methyl), chitosan, silver, magnetic particles, gelatin spheres) can be injected into the diverticulum to plug and prevent fecal entrapment. In one example, the filling material can be biodegradable. In one example, the occluding material is not biodegradable.

Figures 34A, 34B:
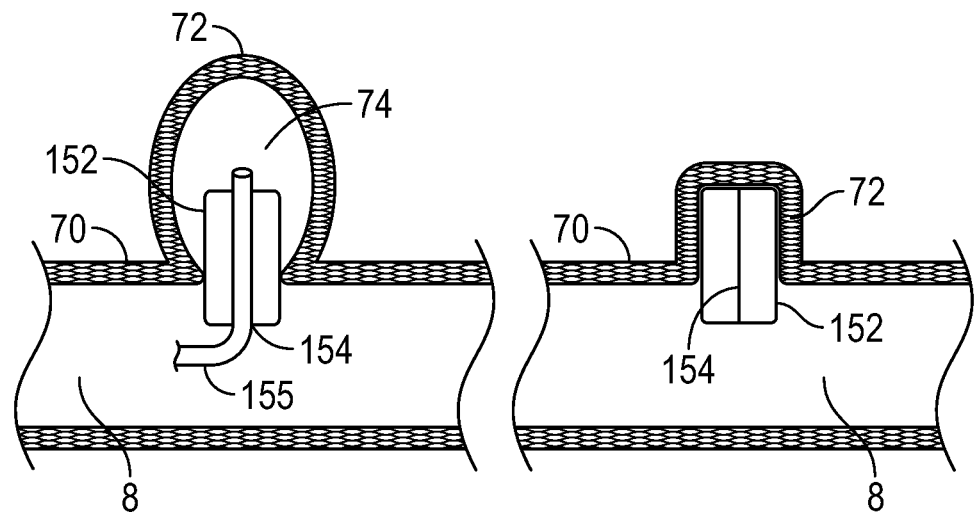
FIGS. 34A and 34B illustrate a schematic representation of a tubular device positioned partially within the diverticulum, in accordance with one example of the present disclosure.

Referring now to FIGS. 34A and 34B, a tubular device 152 (also referred herein as "device 152") for occluding the diverticulum 70 is shown. As seen in FIG. 33A, the device 152 can be inserted partially into the cavity 74 of the diverticulum 72. The device 152 can include a flexible seal 154. The flexible seal 154 can be opened to allow a suction device 155 to extend through the device 154 and apply suction to the cavity 74. As the suction is applied, the diverticulum 72 collapses onto the device 154. In one example, the external surface of the device 154 can include, for example, but not limited to, a biocompatible adhesive, to adhere the collapsed diverticulum 72 onto the device 154. Once the suction device 155 is removed, as illustrated in FIG. 34B, the flexible seal 154 closes and prevents any material from entering the device 152. Thus, the device 152 acts like a plug to occlude the diverticulum and prevent material from becoming entrapped within the diverticulum 72. The device 152 can be biodegradable or non-biodegradable.

Figure 35:
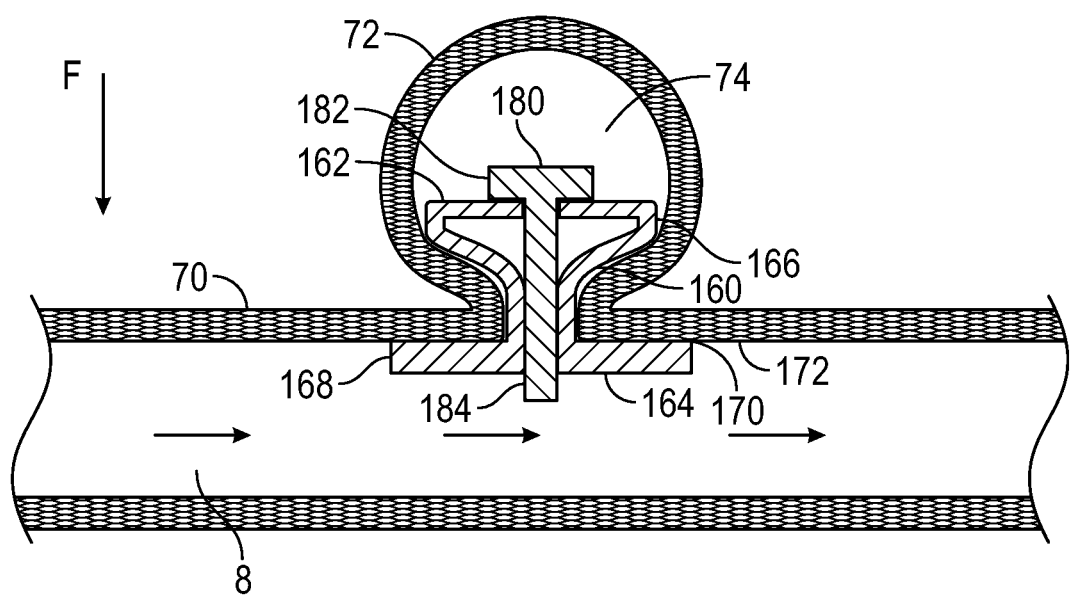
FIG. 35 illustrates a schematic representation of a rivet positioned partially within the diverticulum, in accordance with one example of the present disclosure

Referring to FIG. 35, a rivet 160 occluding the diverticulum 72 is illustrated. As seen in FIG. 35, the rivet 160 includes a first portion 164 and a second portion 180 that can couple together and occlude the diverticulum 72. The first portion 164 includes a flange 168 that when in a final position has an undersurface 170 that contacts the colon inner wall 172. The second portion 180 engages an end 162 of the first portion 164 and as force is applied in direction "F" along the second portion 164 the end 162 of the first portion 164 deforms and forms a projection 166 that engages the diverticulum 72. Once connected, the rivet 160 occludes the diverticulum 72 and can prevent unwanted material from entering the diverticulum 72. In one example, the space above the rivet 160 can be filled with occluding materials, such as materials 150 as discussed herein, or a plurality of particles 56. For example, the space above the rivet 160 can include magnetic particles, non-magnetic particles, biodegradable particles, and non-biodegradable particles, as discussed herein.

Figure 36:
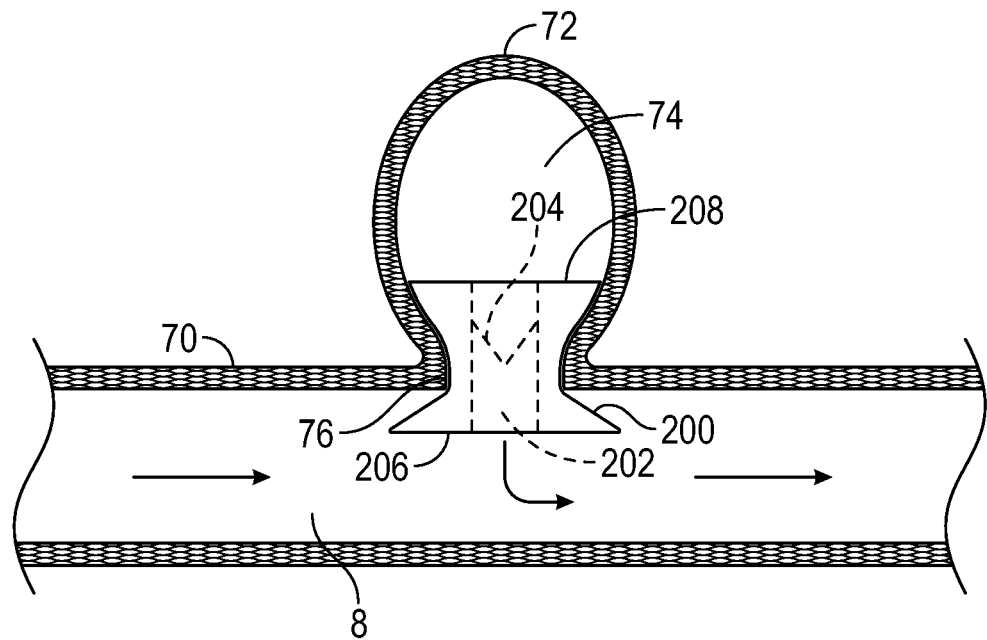
FIG. 36 illustrates a schematic representation of a one-way vale positioned partially within the diverticulum, in accordance with one example of the present disclosure
Figure 37:
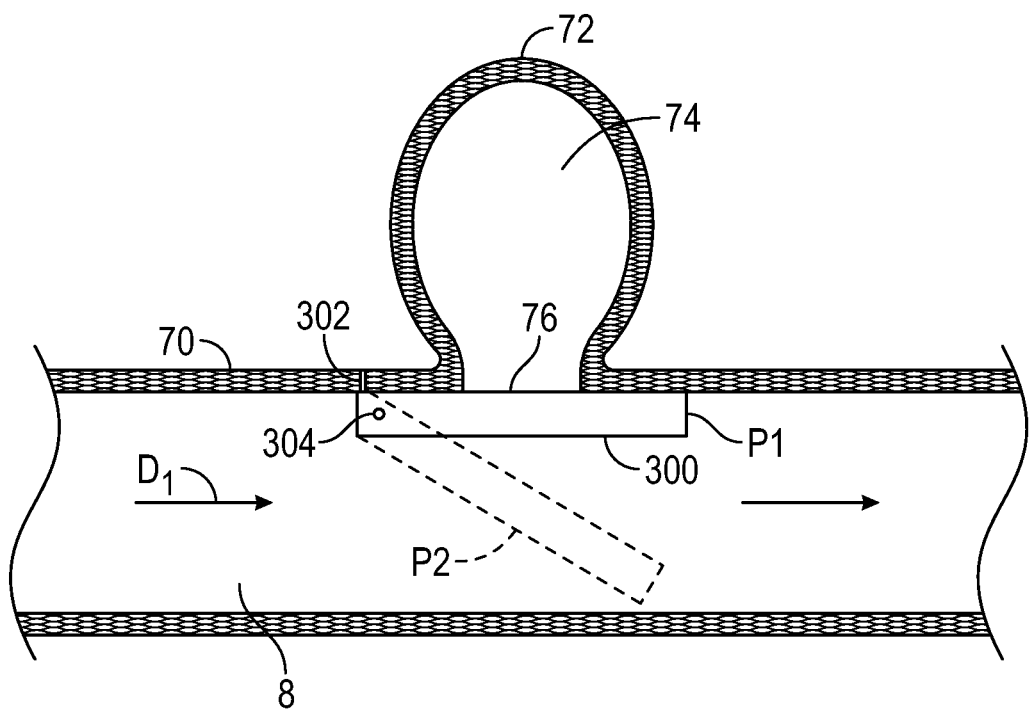
FIG. 37 illustrates a schematic representation of a one-way valve attached to a wall of the colon adjacent to the diverticulum, in accordance with one example of the present disclosure

Referring now to FIGS. 36-37, devices that allow one-way flow from the diverticulum 72 to the colon lumen 8 are illustrated. FIG. 36 illustrates a stent 200 that can be positioned within an ostia 76 of a diverticulum 72. The stent 200 can include a lumen 202 and a one-way valve 204 that allows for one-way flow of material from the diverticulum 72 to the colon lumen 8.

In one example, the stent 200 can be made of plastic such as, but not limited to, Teflon, polyethylene, polyurethane, polyflex, or other materials. In one example, the stent 200 can be made of metal such as, but not limited to, stainless steel, nickel-titanium alloy, cobalt-tungsten alloy, cobalt-chromium alloy, tantalum alloy, gold, titanium, or other materials. The shape of the stent 200 can be one such that the stent 200 is frictionally retained within the diverticulum 72. In one example, the stent 200 is positioned within the ostia 76 of the diverticulum 72 such that a first portion of the stent 200 is within the diverticulum 72 and a second portion of the stent 200 is within the colon lumen 8. The stent 200 can be malleable such that the shape can be adjusted during deployment according to the particular diverticulum 72 being treated.

In one example, the stent 200 can be made of a bioabsorbable material such as Vicryl (polyglactin 910), polyester, polyorthoester, polyanhydride, collagen, or other biodegradable materials. In one embodiment the stent 200 can be absorbed in a number of days to a number of week or months.

In one example, the stent 200 can be made of a rigid material, such as a plastic, polymer, or metal. In one example, the stent 200 can be made of an elastic material, such as certain plastics, polymers, or metals with flexible characteristics. In one example, the stent 200 can be made of a shape memory material, such as Nitinol. In one embodiment, an elastic or deformable stent 200 can have a first configuration and a second configuration. For example, the first configuration can allow the stent 200 to pass through the diverticulum 72 and in the second configuration the stent 200 can expand to a predetermined shape, e.g., but limited to, the hour-glass shape shown in FIG. 36. Additionally, the surface of the stent can include a biocompatible adhesive to further secure the stent to the diverticulum 72.

In one example, the stent 200 can be at least partially coated with a drug coating to release or elute therapeutic agents, such as an antibiotic, an antimicrobial agent, a growth factors, a growth inhibitors, an antiseptic agent, an anti-inflammatory agent, an antirestinosis agent, or an antioxidant.

As shown in FIG. 36, the stent 200 can have a valve 204 disposed in the lumen 202. In one embodiment the valve 204 is disposed between the proximal end 208 and the distal end 210 of the stent 200. In one example, the vale 204 is located at or near the proximal end 206. In one example, the valve 204 is located at or near the distal end 210. In one embodiment the valve 204 is a one-way valve that allows fluid or particle flow in one direction and reduces or eliminates flow in the opposite direction. In one embodiment the valve 200 is a one-way valve that promotes drainage of the diverticulum 72.

In one example, the valve 204 can be a duck-bill valve. In one example, the valve 204 has two or more opposed surfaces that can touch each other to occlude or restrict the lumen 202, and that can be actuated by pressure differential between the proximal end 206 and the distal end 208 of the stent 200. As shown in FIG. 36 the valve 200 can be configured to allow flow from the distal lumen section 208 to the proximal lumen section 206.

In one example, the space above the stent 200 can be filled with occluding materials, such as materials 150 as discussed herein, or a plurality of particles 56. For example, the space above the stent 200 can include magnetic particles, non-magnetic particles, biodegradable particles, and non-biodegradable particles, as discussed herein.

FIG. 37 illustrates a valve 300 that can be positioned over an ostia 76 of a diverticulum 72. The valve 300 can be plate-like and be coupled to the colon 700 via, e.g., but not limited to, sutures 302. The dimensions and position of the valve 300 should be such that when the valve 300 is in a closed position "P1", the ostia 76 is completely covered. The valve 300 can rotate about rotation point 304 to allow material to flow from the cavity of the diverticulum 72 to the colon lumen 8. As material passes the valve 300 in direction D1, the valve 300 can rotate from an open position "P2" to the closed positioned "P1". The valve 300 can be formed from the same materials discussed herein with regard to the stent 200.

In one example, the diverticulum can be filled with occluding materials, such as materials 150 as discussed herein, or a plurality of particles 56. For example, the space above the stent 200 can include magnetic particles, non-magnetic particles, biodegradable particles, and non-biodegradable particles, as discussed herein.

Figure 38:
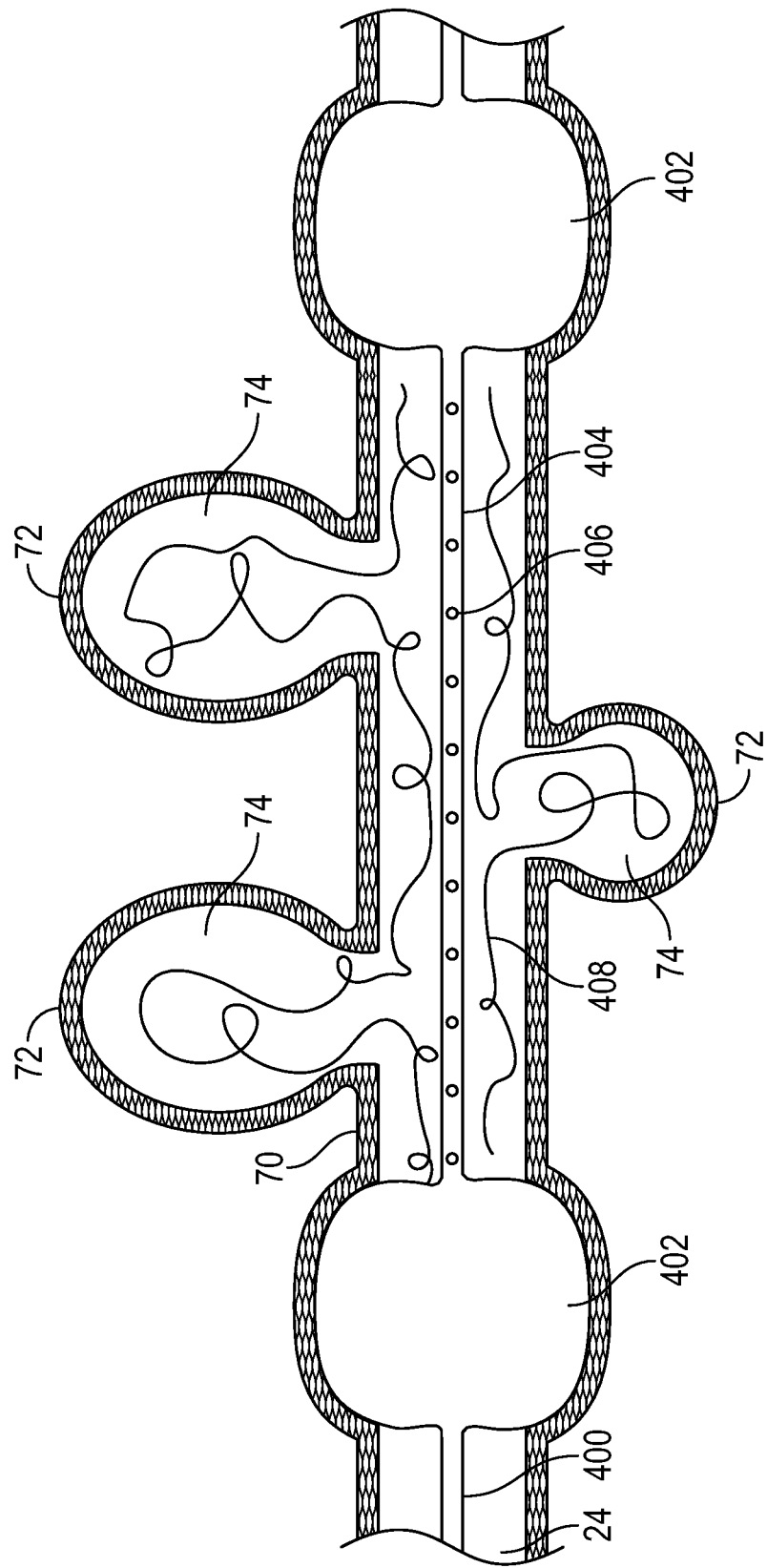
FIG. 38 illustrates a schematic representation of a device positioned within the colon for treating one or more diverticulum at a time, in accordance with one example of the present disclosure

FIG. 38 illustrates a method of treating more than one diverticulum 72 at a time. For example, a flexible conduit 400 including at least two balloon-forming chambers 402 and a perforated flexible conduit 404 positioned between the two balloon-forming chambers 402. The balloon-forming chambers 402 can be introduced into the colon lumen 8 and positioned such that the diverticulum 72 to be treated are positioned between the two balloon-forming chambers 402. The balloon-forming chambers 402 can be inflated to seal off the one or more diverticulum 72 positioned between the two balloon-forming chambers 402. A material 408 can be introduced into the perforated flexible conduit 404 such that the material 408 flows through openings 406 of the perforated flexible conduit 404 and into a portion of the colon lumen 8. As the material 408 continues to be introduced, the pressure increases within the sealed off portion and the diverticulum 72 can expand and/or get flushed out with the material 408. One or more materials 408 can be used to flush out the diverticulum 72 multiple times. In one example, the balloon-forming chambers 402 and the perforated flexible conduit 404 are in fluid communication. In one embodiment, the balloon-forming chambers 402 and the perforated flexible conduit 404 are not in fluid communication.

VARIOUS NOTES & EXAMPLES

Example 1 a method of treating diverticulitis, the method comprising: placing an endoscopic device within a colonic lumen relative to a diverticulum; advancing a delivery shaft from the endoscopic device and into the diverticulum; and releasing a plurality of particles into the diverticulum, wherein the plurality of particles include one or more therapeutic agents to treat the diverticulitis and form a cluster formation to at least partially occlude the diverticulum.

Example 2 can include, or can optionally be combined with the subject matter of Example 1, to optionally include where the plurality of particles includes a plurality of magnetized particles and a plurality of non-magnetized particles.

Example 3 can include, or can optionally be combined with the subject matter of one or any combination of Examples 1 or 2 to optionally include where at least a portion of the plurality of the magnetized particles include a magnetic core and at least one of an antimicrobial coating and a therapeutic coating.

Example 4 can include, or can optionally be combined with the subject matter of one or any combination of Examples 1 through 3 to optionally include where the antimicrobial coating is positioned between the magnetic core and the therapeutic coating.

Example 5 can include, or can optionally be combined with the subject matter of one or any combination of Examples 1 through 4 to optionally include where the therapeutic coating is biodegradable.

Example 6 can include, or can optionally be combined with the subject matter of one or any combination of Examples 1 through 5 to optionally include where the antimicrobial coating includes silver.

Example 7 can include, or can optionally be combined with the subject matter of one or any combination of Examples 1 through 6 to optionally include where the plurality of non-magnetized particles include bio-degradable medicated particles.

Example 8 can include, or can optionally be combined with the subject matter of one or any combination of Examples 1 through 7 to optionally include where, prior to releasing the plurality of particles, the method further includes: positioning a stent in within the diverticulum, the stent including a bioadhesive; expanding the stent to contact and adhere to an inner surface of the diverticulum; and after releasing the plurality of particles, collapsing the stent around the plurality of particles.

Example 9 can include, or can optionally be combined with the subject matter of one or any combination of Examples 1 through 8 to optionally include wherein, prior to releasing the plurality of particles, the method further includes at least one of: aspirating the diverticulum utilizing an aspiration device in operable cooperation with the endoscopic device, the aspiration device configured to suction the undesirable material from the at least one diverticulum; and irrigating the at least one diverticulum utilizing an irrigation device in operable cooperation with the endoscopic device, the lavage device configured to utilize fluid to flush out the at least one diverticulum.

Example 10 can include, or can optionally be combined with the subject matter of one or any combination of Examples 1 through 9 to optionally include a system for treating diverticulitis, comprising: a plurality of particles configured to be injected into a diverticulum, wherein the plurality of particles includes: a plurality of magnetized particles having a magnetic core and at least an antimicrobial coating.

Example 11 can include, or can optionally be combined with the subject matter of one or any combination of Examples 1 through 10 to optionally include where at least a portion of the plurality of magnetized particles further include a biodegradable therapeutic coating.

Example 12 can include, or can optionally be combined with the subject matter of one or any combination of Examples 1 through 11 to optionally include where the plurality of particles further includes a plurality of biodegradable particles including a therapeutic agent.

Example 13 can include, or can optionally be combined with the subject matter of one or any combination of Examples 1 through 12 to optionally include where the therapeutic agent is selected from at least one of an antibiotic agent, beneficial flora, an antimicrobial agent, growth factors, growth inhibitors, an antiseptic agent, an anti-inflammatory agent, an antirestinosis agent, or an antioxidant.

Example 14 can include, or can optionally be combined with the subject matter of one or any combination of Examples 1 through 13 to optionally include the antimicrobial coating includes silver.

Example 15 can include, or can optionally be combined with the subject matter of one or any combination of Examples 1 through 14 to optionally include where the plurality of magnetized particles include: a main particle having a first maximum dimension, the main particle being selectively magnetized to include a plurality of magnetic attachment locations; and a plurality of attachment particles having a second maximum dimension that is less than the first maximum dimension, wherein the plurality of attachment particles adhere together to form arms that adhere to the main particle at the plurality of magnetic attachment locations.

Example 16 can include, or can optionally be combined with the subject matter of one or any combination of Examples 1 through 15 to optionally include where the plurality of magnetized particles include: a main particle having an outer surface having a plurality of openings extending from the outer surface to a cavity; a magnetic particle positioned within the cavity of the main particle; and a plurality of attachment particles having a size less than a size of the plurality of openings, wherein the magnetic particle is configured to attract the plurality of attachment particles such that the plurality of attachment particles are configured to move through the openings and attach to the magnetic particle.

Example 17 can include, or can optionally be combined with the subject matter of one or any combination of Examples 1 through 16 to optionally include an endoscopic device including a deliver shaft having a flexible tip that is configured to release a single particle of the plurality of particles at a time.

Example 18 can include, or can optionally be combined with the subject matter of one or any combination of Examples 1 through 17 to optionally include a method of treating diverticulitis, the method comprising: advancing a delivery shaft from an endoscopic device positioned within a colonic lumen and into the diverticulum; and releasing a plurality of magnetic particles into the diverticulum, wherein the plurality of magnetic particles have a predetermined cluster formation, the predetermined cluster formation having at least one dimension that is greater than a dimension of an ostia of the diverticulum.

Example 19 can include, or can optionally be combined with the subject matter of one or any combination of Examples 1 through 18 to optionally include where at least a portion of the plurality of the magnetized particles include a magnetic core and at least one of an antimicrobial coating and a therapeutic coating.

Example 20 can include, or can optionally be combined with the subject matter of one or any combination of Examples 1 through 19 to optionally include releasing a plurality of non-magnetic biodegradable medicated particles into the diverticulum.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A method of treating diverticulitis, the method comprising:
   placing an endoscopic device within a colonic lumen relative to a diverticulum;
   advancing a delivery shaft from the endoscopic device and into the diverticulum; and
   releasing a plurality of particles into the diverticulum, wherein the plurality of particles includes a plurality of magnetized particles, a plurality of non-magnetized particles and one or more therapeutic agents to treat the diverticulitis and form a cluster formation to at least partially occlude the diverticulum.

2. The method of claim 1, wherein at least a portion of the plurality of the magnetized particles include a magnetic core and at least one of an antimicrobial coating and a therapeutic coating.

3. The method of claim 2, wherein the antimicrobial coating is positioned between the magnetic core and the therapeutic coating.

4. The method of claim 3, wherein the therapeutic coating is biodegradable.

5. The method of claim 3, wherein the antimicrobial coating includes silver.

6. The method of claim 1, wherein the plurality of non-magnetized particles include bio-degradable medicated particles.

7. The method of claim 1, wherein, prior to releasing the plurality of particles, the method further includes:
   positioning a stent in within the diverticulum, the stent including a bioadhesive;
   expanding the stent to contact and adhere to an inner surface of the diverticulum; and after releasing the plurality of particles, collapsing the stent around the plurality of particles.

8. The method of claim 1, wherein, prior to releasing the plurality of particles, the method further includes at least one of:
aspirating the diverticulum utilizing an aspiration device in operable cooperation with the endoscopic device, the aspiration device configured to suction undesirable material from the at least one diverticulum; and
irrigating the at least one diverticulum utilizing an irrigation device in operable cooperation with the endoscopic device, a lavage device configured to extend distally from the endoscopic device and to utilize fluid to flush out the at least one diverticulum.

9. The method of treating diverticulitis of claim 1, including:
forming the plurality of particles into an agglomeration, at least a portion of the plurality of particles includes the one or more therapeutic agents;
retaining the agglomeration within the diverticulum; and
while retaining the agglomeration within the diverticulum releasing the one or more therapeutic agents.

10. A system for treating diverticulitis, comprising:
a plurality of particles configured to be injected into a diverticulum, wherein the plurality of particles includes:
a plurality of magnetized particles having a magnetic core and at least an antimicrobial coating.

11. The system of claim 10, wherein at least a portion of the plurality of magnetized particles further include a biodegradable therapeutic coating.

12. The system of claim 10, wherein the plurality of particles further includes a plurality of biodegradable particles including a therapeutic agent.

13. The system of claim 12, wherein the therapeutic agent is selected from at least one of an antibiotic agent, beneficial flora, an antimicrobial agent, growth factors, growth inhibitors, an antiseptic agent, an anti-inflammatory agent, an antirestinosis agent, or an antioxidant.

14. The system of claim 10, wherein the antimicrobial coating includes silver.

15. The system of claim 10, wherein the plurality of magnetized particles include:

a main particle having a first maximum dimension, the main particle being selectively magnetized to include a plurality of magnetic attachment locations; and
a plurality of attachment particles having a second maximum dimension that is less than the first maximum dimension, wherein the plurality of attachment particles adhere together to form arms that adhere to the main particle at the plurality of magnetic attachment locations.

16. The system of claim 10, wherein the plurality of magnetized particles include:
a main particle having an outer surface having a plurality of openings extending from the outer surface to a cavity;
a magnetic particle positioned within the cavity of the main particle; and
a plurality of attachment particles having a size less than a size of the plurality of openings,
wherein the magnetic particle is configured to attract the plurality of attachment particles such that the plurality of attachment particles are configured to move through the openings and attach to the magnetic particle.

17. The system of claim 10, further including:
an endoscopic device including a deliver shaft having a flexible tip that is configured to release a single particle of the plurality of particles at a time.

18. A method of treating diverticulitis, the method comprising:
advancing a delivery shaft from an endoscopic device positioned within a colonic lumen and into a diverticulum; and
releasing a plurality of magnetic particles into the diverticulum, wherein the plurality of magnetic particles have a predetermined cluster formation, the predetermined cluster formation having at least one dimension that is greater than a dimension of an ostia of the diverticulum.

19. The method of claim 18, wherein at least a portion of the plurality of the magnetized particles include a magnetic core and at least one of an antimicrobial coating and a therapeutic coating.

20. The method of claim 18, including:
releasing a plurality of non-magnetic biodegradable medicated particles into the diverticulum.

* * * * *